United States Patent
Sakanishi et al.

(10) Patent No.: US 11,078,181 B2
(45) Date of Patent: Aug. 3, 2021

(54) DIARYL PYRAZOLE COMPOUND AND FORMULATION FOR CONTROLLING HARMFUL ORGANISMS

(71) Applicant: Nippon Soda Co., Ltd., Tokyo (JP)

(72) Inventors: Keita Sakanishi, Odawara (JP); Takao Iwasa, Odawara (JP); Norifumi Sakiyama, Odawara (JP); Hikaru Aoyama, Odawara (JP); Tomomi Kobayashi, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 171 days.

(21) Appl. No.: 16/469,937

(22) PCT Filed: Dec. 14, 2017

(86) PCT No.: PCT/JP2017/044836
§ 371 (c)(1),
(2) Date: Jun. 14, 2019

(87) PCT Pub. No.: WO2018/116945
PCT Pub. Date: Jun. 28, 2018

(65) Prior Publication Data
US 2019/0359588 A1    Nov. 28, 2019

(30) Foreign Application Priority Data

Dec. 19, 2016  (JP) .............................. JP2016-245530

(51) Int. Cl.
| C07D 401/04 | (2006.01) |
| C07D 401/14 | (2006.01) |
| A01N 43/56 | (2006.01) |
| A01N 43/653 | (2006.01) |

(52) U.S. Cl.
CPC ........... *C07D 401/04* (2013.01); *A01N 43/56* (2013.01); *A01N 43/653* (2013.01); *C07D 401/14* (2013.01)

(58) Field of Classification Search
CPC .... C07D 401/04; C07D 401/14; A01N 43/56; A01N 43/653
See application file for complete search history.

(56) References Cited

U.S. PATENT DOCUMENTS

| 2011/0021539 A1 | 1/2011 | Schwarz et al. |
| 2012/0190687 A1 | 7/2012 | Schwarz et al. |
| 2016/0278379 A1 | 9/2016 | Hallenbach et al. |
| 2018/0160686 A1 | 6/2018 | Aoyama et al. |
| 2018/0362470 A1 | 12/2018 | Hamamoto et al. |

FOREIGN PATENT DOCUMENTS

| JP | 2016-536364 A | 11/2016 |
| WO | WO-2010/136145 A1 | 12/2010 |
| WO | WO-2016/113155 A1 | 7/2016 |
| WO | WO-2016/204270 A1 | 12/2016 |
| WO | WO-2017/104741 A1 | 6/2017 |

OTHER PUBLICATIONS

International Search Report dated Mar. 13, 2018, in PCT/JP2017/044836.

*Primary Examiner* — Zohreh A Fay
(74) *Attorney, Agent, or Firm* — Foley & Lardner LLP

(57) ABSTRACT

A compound represented by the following Formula (I) or a salt thereof, as well as a formulation for controlling harmful organisms, and in particular, an insecticidal formulation, a miticidal formulation, a formulation for controlling ectoparasites or a formulation for controlling or killing endoparasites, which contains at least one compound selected from the compounds of Formula (I) and salts thereof as an active ingredient (I)

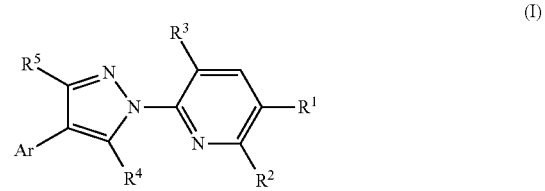

wherein, each of $R^1$ and $R^2$ independently represents a hydrogen atom, a substituted or unsubstituted C1-6 alkyl group, or the like, with the proviso that when $R^2$ represents a hydrogen atom, $R^1$ represents a substituted or unsubstituted C6-10 aryl group or a substituted or unsubstituted 3- to 6-membered heterocyclyl group; $R^3$ represents a C1-6 alkylthio group or the like; each of $R^4$ and $R^5$ independently represents a hydrogen atom, a halogeno group or the like; and Ar represents a substituted or unsubstituted C6-10 aryl group, or a substituted or unsubstituted 5- to 6-membered heteroaryl group.

5 Claims, No Drawings

DIARYL PYRAZOLE COMPOUND AND FORMULATION FOR CONTROLLING HARMFUL ORGANISMS

TECHNICAL FIELD

The present invention relates to a diaryl pyrazole compound and a formulation for controlling harmful organisms. In particular, the present invention relates to a diaryl pyrazole compound which has superior insecticidal activity and/or acaricidal activity, exhibits superior safety, and can be industrially-advantageously synthesized, and also relates to a formulation for controlling harmful organisms containing the same as an active ingredient.

This application is a National Stage application of PCT/JP/2017/044836, filed Dec. 14, 2017, which claims priority on the basis of Japanese Patent Application No. 2016-245530, filed on Dec. 19, 2016 in Japan, the content of which is incorporated herein by reference.

BACKGROUND ART

Various compounds having an insecticidal and/or acaricidal activity have been proposed. In order to practically use such compounds as agrochemicals, the compounds are required not only to have a sufficient efficacy, but also to hardly cause chemical resistance, avoid phytotoxicity against plants or soil contamination, and have a low level of toxicity against livestock, fish or the like.

Patent Document 1 discloses a compound represented by Formula (a). Patent Document 1 describes that the compound mentioned above has an insecticidal and/or acaricidal activity.

[Chem. 1]

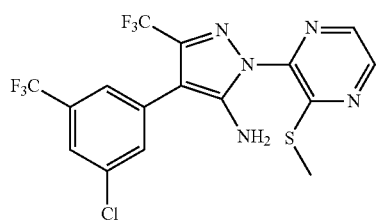

(a)

Patent Document 2 discloses a compound represented by Formula (b). Patent Document 2 describes that the compound mentioned above has an insecticidal and/or acaricidal activity.

[Chem. 2]

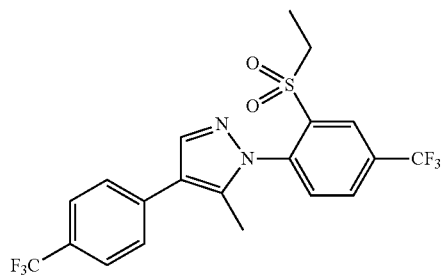

(b)

Patent Document 3 discloses a compound represented by Formula (c). Patent Document 3 describes that the compound mentioned above has an insecticidal and/or acaricidal activity.

[Chem. 3]

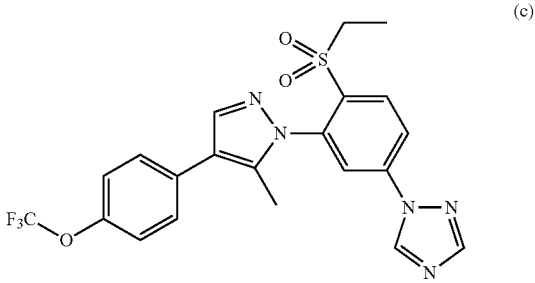

(c)

PRIOR ART LITERATURE

Patent Documents

[Patent Document 1] PCT international Publication No. WO2010/136145
[Patent Document 2] PCT international Publication No. WO2016/113155
[Patent Document 3] PCT international Publication No. WO2016/204270

DISCLOSURE OF INVENTION

Technical Problem

An object of the present invention is to provide a diaryl pyrazole compound which has superior activity for controlling harmful organisms, and in particular, superior insecticidal activity and/or acaricidal activity, exhibits superior safety, and can be industrially-advantageously synthesized, as well as to provide a formulation for controlling harmful organisms containing the same as an active ingredient. In addition, a further object of the invention is to provide a formulation for controlling ectoparasites or a formulation for controlling or expelling endoparasites which contains the same as an active ingredient.

Solution to Problem

As a result of diligent studies in order to achieve the objects mentioned above, the inventors of the present application completed the present invention including the following modes.

[1] A compound represented by Formula (I) or a salt thereof.

[Chem. 4]

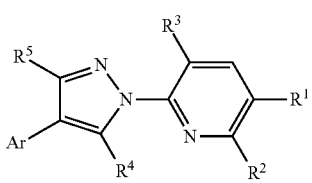

(I)

wherein each of $R^1$ and $R^2$ independently represents a hydrogen atom, a substituted or unsubstituted C1-6 alkyl group, a substituted or unsubstituted C2-6 alkenyl group, a substituted or unsubstituted C2-6 alkynyl group, a hydroxyl group, a substituted or unsubstituted C1-6 alkoxy group, a formyl group, a substituted or unsubstituted C1-6 alkyl carbonyl group, a substituted or unsubstituted C1-6 alkoxy carbonyl group, a mercapto group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted aminocarbonyl group, a substituted or unsubstituted C3-8 cycloalkyl group, a substituted or unsubstituted C6-10 aryl group, a substituted or unsubstituted C6-10 aryloxy group, a substituted or unsubstituted 3- to 6-membered heterocyclyl group, a substituted or unsubstituted amino group, a halogeno group, a cyano group, or a nitro group, with the proviso that in the case of $R^1$ being a hydrogen atom, $R^1$ is a substituted or unsubstituted C6-10 aryl group, or a substituted or unsubstituted 3- to 6-membered heterocyclyl group, $R^3$ represents a substituted or unsubstituted C1-6 alkylthio group, a substituted or unsubstituted C1-6 alkylsulfinyl group, a substituted or unsubstituted C1-6 alkylsulfonyl group, a substituted or unsubstituted C1-6 alkylsulfonyloxy group, or a group represented by —S(=O)(=N—$R^a$)—$R^b$, in which each of $R^a$ and $R^b$ independently represents a substituted or unsubstituted C1-6 alkyl group, each of $R^4$ and $R^5$ independently represents a hydrogen atom, a halogeno group, a cyano group, a substituted or unsubstituted C1-6 alkyl group, a substituted or unsubstituted C2-6 alkenyl group, a substituted or unsubstituted C2-6 alkynyl group, a hydroxyl group, a substituted or unsubstituted C1-6 alkoxy group, a formyl group, a substituted or unsubstituted C1-6 alkyl carbonyl group, a substituted or unsubstituted C1-6 alkoxy carbonyl group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C1-6 alkylsulfonyloxy group, a substituted or unsubstituted amino group, or a group represented by —S(=O)(=N—$R^a$)—$R^b$, in which each of $R^a$ and $R^b$ independently represents a substituted or unsubstituted C1-6 alkyl group, and Ar represents a substituted or unsubstituted C6-10 aryl group, or a substituted or unsubstituted, 5- to 6-membered heteroaryl group.

[2] The compound according to [1] mentioned above or a salt thereof, wherein $R^1$ represents a hydrogen atom, $R^1$ represents a substituted or unsubstituted C6-10 aryl group, or a substituted or unsubstituted 3- to 6-membered heterocyclyl group, $R^3$ represents a C1-6 alkylsulfonyl group, $R^4$ represents a C1-6 alkyl group, or a substituted or unsubstituted amino group, and $R^5$ represents a hydrogen atom.

[3] The compound according to [1] mentioned above or a salt thereof, wherein $R^1$ represents a substituted or unsubstituted C6-10 aryl group, or a substituted or unsubstituted 3- to 6-membered heterocyclyl group, $R^1$ represents a hydrogen atom, $R^3$ represents a C1-6 alkylsulfonyl group, $R^4$ represents a C1-6 alkyl group, or a substituted or unsubstituted amino group, and $R^5$ represents a hydrogen atom.

[4] A formulation for controlling harmful organisms, containing at least one compound selected from the group consisting of the compounds as recited in any one of [1] to [3] mentioned above and salts thereof, as an active ingredient.

[5] An insecticidal formulation or an acaricidal formulation, containing at least one compound selected from the group consisting of the compounds as recited in any one of [1] to [3] mentioned above and salts thereof, as an active ingredient.

[6] A formulation for controlling ectoparasites, containing at least one compound selected from the group consisting of the compounds as recited in any one of [1] to [3] mentioned above and salts thereof, as an active ingredient.

[7] A formulation for controlling endoparasites or for expelling endoparasites, containing at least one compound selected from the group consisting of the compounds as recited in any one of [1] to [3] mentioned above and salts thereof, as an active ingredient.

Advantageous Effects of the Invention

The diaryl pyrazole compounds of the present invention can control harmful organisms which are problematic in view of farm products or for hygiene reasons. In particular, the compounds can effectively control various types of agricultural pests and acari with a reduced concentration. In addition, the diaryl pyrazole compounds of the present invention can effectively control ectoparasites and endoparasites which harm humans and animals.

EMBODIMENTS OF THE INVENTION

[Diaryl Pyrazole Compounds]

A diaryl pyrazole compound of the present invention is a compound represented by Formula (I) (hereinafter, referred to as compound (I) in some cases) or a salt of compound (I).

[Chem. 5]

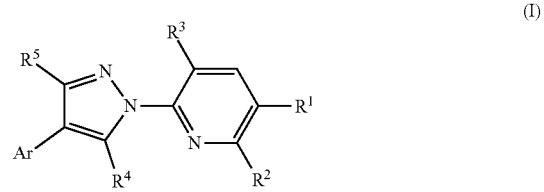

(I)

In the present invention, the term "unsubstituted" means that only a group which is a mother nucleus is present. When only the name of a group as a mother nucleus is described without the term "substituted", it means "unsubstituted" unless otherwise specified.

On the other hand, the term "substituted (=having a substituent)" means that at least one hydrogen atom of a group as a mother nucleus is substituted with a group having a structure which is the same as or different from the mother nucleus. Therefore, a "substituted group (substituent)" is another group which is bonded to the group as the mother nucleus. The substituted group may be one, or may be two or more. Two or more substituted groups may be the same as or different from each other.

The term "C1-6" represents that the number of carbon atoms of a group as a mother nucleus is 1 to 6. The number of carbon atoms does not include the number of carbon atoms present in a substituted group. For example, a butyl group having an ethoxy group as a substituted group is classified as a C2 alkoxy C4 alkyl group.

A "substituted group" is not particularly limited as long as it is chemically acceptable and has the effect of the present invention. Hereinafter, as examples of a group which can be a "substituted group", mention may be made of, a C1-6 alkyl group such as a methyl group, an ethyl group, an n-propyl group, an i-propyl group, an n-butyl group, an s-butyl group, an i-butyl group, a t-butyl group, an n-pentyl group, or an n-hexyl group;

a C2-6 alkenyl group such as a vinyl group, a 1-propenyl group, a 2-propenyl group (an allyl group), a 1-butenyl group, a 2-butenyl group, a 3-butenyl group, a 1-methyl-2-propenyl group, or a 2-methyl-2-propenyl group;

a C2-6 alkynyl group such as an ethynyl group, a 1-propynyl group, a 2-propynyl group, a 1-butynyl group, a 2-butynyl group, a 3-butynyl group, or a 1-methyl-2-propynyl group;

a C3-8 cycloalkyl group such as a cyclopropyl group, a cyclobutyl group, a cyclopentyl group, a cyclohexyl group, or a cubanyl group;

a C6-10 aryl group such as a phenyl group, or a naphthyl group;

a C6-10 aryl C1-6 alkyl group such as a benzyl group, or a phenethyl group;

a 3- to 6-membered heterocyclyl group;

a 3- to 6-membered heterocyclyl C1-6 alkyl group;

a hydroxyl group;

a C1-6 alkoxy group such as a methoxy group, an ethoxy group, an n-propoxy group, an i-propoxy group, an n-butoxy group, an s-butoxy group, an i-butoxy group, or a t-butoxy group;

a C2-6 alkenyloxy group such as a vinyloxy group, an allyloxy group, a propenyloxy group, or a butenyloxy group;

a C2-6 alkynyloxy group such as an ethynyloxy group, or a propargyloxy group;

a C6-10 aryloxy group such as a phenoxy group, or a naphthoxy group;

a C6-10 aryl C1-6 alkoxy group such as a benzyloxy group, or a phenethyloxy group;

a 5- to 6-membered heteroaryloxy group such as a thiazolyloxy group, or a pyridyloxy group;

a 5- to 6-membered heteroaryl C1-6 alkyloxy group such as a thiazolyl methyloxy group, or a pyridyl methyloxy group;

a formyl group;

a C1-6 alkyl carbonyl group such as an acetyl group, or a propionyl group;

a formyloxy group;

a C1-6 alkyl carbonyloxy group such as an acetyloxy group, or a propionyloxy group;

a C6-10 aryl carbonyl group such as a benzoyl group;

a C1-6 alkoxy carbonyl group such as a methoxycarbonyl group, an ethoxycarbonyl group, an n-propoxycarbonyl group, an i-propoxycarbonyl group, an n-butoxycarbonyl group, or a t-butoxycarbonyl group;

a C1-6 alkoxy carbonyloxy group such as a methoxycarbonyloxy group, an ethoxycarbonyloxy group, an n-propoxycarbonyloxy group, an i-propoxycarbonyloxy group, an n-butoxycarbonyloxy group, or a t-butoxycarbonyloxy group;

a carboxyl group;

a halogeno group such as a fluoro group, a chloro group, a bromo group, or an iodo group;

a C1-6 haloalkyl group such as a chloromethyl group, a chloroethyl group, a difluoromethyl group, a trifluoromethyl group, a 2,2,2-trifluoroethyl group, a perfluoroethyl group, a 1,2-dichloro-n-propyl group, a 1-fluoro-n-butyl group, or a perfluoro-n-pentyl group;

a C2-6 haloalkenyl group such as a 2-chloro-1-propenyl group, or a 2-fluoro-1-butenyl group;

a C2-6 haloalkynyl group such as a 4,4-dichloro-1-butynyl group, a 4-fluoro-1-pentynyl group, or a 5-bromo-2-pentynyl group;

a C1-6 haloalkoxy group such as a trifluoromethoxy group, a 2-chloro-n-propoxy group, or a 2,3-dichlorobutoxy group;

a C2-6 haloalkenyloxy group such as a 2-chloropropenyloxy group, or a 3-bromobutenyloxy group;

a C1-6 haloalkyl carbonyl group such as a chloroacetyl group, a trifluoroacetyl group, or a trichloroacetyl group;

an amino group;

a C1-6 alkyl substituted amino group such as a methylamino group, a dimethylamino group, or a diethylamino group;

a C6-10 aryl amino group such as an anilino group, or a naphthyl amino group;

a C6-10 aryl C1-6 alkyl amino group such as a benzylamino group, or a phenethyl amino group;

a formylamino group;

a C1-6 alkyl carbonylamino group such as an acetylamino group, a propanoylamino group, a butyrylamino group, or an i-propyl carbonyl amino group;

a mono(C1-6 alkoxy carbonyl) amino group such as a methoxycarbonyl amino group, an ethoxycarbonyl amino group, an n-propoxycarbonyl amino group, an i-propoxycarbonyl amino group, or a t-butoxycarbonyl amino group;

a di(C1-6 alkoxy carbonyl) amino group such as a di(methoxycarbonyl) amino group, a di(ethoxycarbonyl) amino group, a di(n-propoxycarbonyl) amino group, a di(i-propoxycarbonyl) amino group, a di(n-butoxycarbonyl) amino group, or a di(t-butoxycarbonyl) amino group;

a substituted or unsubstituted aminocarbonyl group such as an aminocarbonyl group, a dimethyl aminocarbonyl group, a phenyl aminocarbonyl group, or an N-phenyl-N-methyl aminocarbonyl group;

an imino C1-6 alkyl group such as an iminomethyl group, a (1-imino)ethyl group, or a (1-imino)-n-propyl group;

a substituted or unsubstituted N-hydroxyimino C1-6 alkyl group such as an N-hydroxy-iminomethyl group, a (1-(N-hydroxy)-imino)ethyl group, a (1-(N-hydroxy)-imino)propyl group, an N-methoxy-iminomethyl group, or a (1-(N-methoxy)-imino)ethyl group;

an aminocarbonyloxy group;

a C1-6 alkyl aminocarbonyloxy group such as an ethyl aminocarbonyloxy group, or a dimethyl aminocarbonyloxy group;

a mercapto group;

a C1-6 alkylthio group such as a methylthio group, an ethylthio group, an n-propylthio group, an i-propylthio group, an n-butylthio group, an i-butylthio group, an s-butylthio group, or a t-butylthio group;

a C1-6 haloalkylthio group such as a trifluoromethylthio group, or a 2,2,2-trifluoroethylthio group;

a C6-10 arylthio group such as a phenylthio group, or a naphthylthio group;

a 5- to 6-membered heteroarylthio group such as a thiazolylthio group, or a pyridylthio group;

a C1-6 alkylsulfinyl group such as a methylsulfinyl group, an ethylsulfinyl group, or a t-butylsulfinyl group;

a C1-6 haloalkylsulfinyl group such as a trifluoromethyl sulfinyl group, or a 2,2,2-trifluoroethyl sulfinyl group;

a C6-10 arylsulfinyl group such as a phenylsulfinyl group;

a 5- to 6-membered heteroarylsulfinyl group such as a thiazolylsulfinyl group, or a pyridylsulfinyl group;

a C1-6 alkylsulfonyl group such as a methylsulfonyl group, an ethylsulfonyl group, or a t-butylsulfonyl group;

a C1-6 haloalkylsulfonyl group such as a trifluoromethyl sulfonyl group, or a 2,2,2-trifluoroethyl sulfonyl group;

a C6-10 arylsulfonyl group such as a phenylsulfonyl group;

a 5- to 6-membered heteroaryl sulfonyl group such as a thiazolylsulfonyl group, or a pyridylsulfonyl group;

a C1-6 alkylsulfonyloxy group such as a methylsulfonyloxy group, an ethylsulfonyloxy group, or a t-butylsulfonyloxy group;

a C1-6 haloalkyl sulfonyloxy group such as a trifluoromethyl sulfonyloxy group, or a 2,2,2-trifluoroethyl sulfonyloxy group;

a tri C1-6 alkyl silyl group such as a trimethylsilyl group, a triethylsilyl group, or a t-butyldimethylsilyl group;

a tri C6-10 aryl silyl group such as a triphenylsilyl group;

a cyano group; and a nitro group.

In addition, any of the hydrogen atoms in these "substituted groups" may be substituted with other substituted groups having a different structure. In this case, examples of the "substituted groups" include a C1-6 alkyl group, a C1-6 haloalkyl group, a C1-6 alkoxy group, a C1-6 haloalkoxy group, a halogeno group, a cyano group, a nitro group and the like.

In addition, the aforementioned "3- to 6-membered heterocyclyl group" is a group having 1 to 4 heteroatoms selected from the group consisting of a nitrogen atom, an oxygen atom and a sulfur atom as a constitutional atom of the ring. The heterocyclyl group may be a monocyclyl group or a polycyclyl group. As long as at least one ring is a hetero ring in the polyheterocyclyl group, the remaining ring may be a saturated alicyclic ring, an unsaturated alicyclic ring or an aromatic ring. Examples of the "3- to 6-membered heterocyclyl group" include a 3- to 6-membered saturated heterocyclyl group, a 5- to 6-membered heteroaryl group, a 5- to 6-membered partially unsaturated heterocyclyl group, and the like.

Examples of the "3- to 6-membered saturated heterocyclyl group" include an aziridinyl group, an epoxy group, a pyrrolidinyl group, a tetrahydrofuranyl group, a thiazolidinyl group, a piperidinyl group, a piperazinyl group, a morpholinyl group, a dioxolanyl group, a dioxanyl group, and the like.

Examples of the "5-membered heteroaryl group" include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, a tetrazolyl group, and the like.

Examples of the "6-membered heteroaryl group" include a pyridyl group, a pyrazinyl group, a pyrimidinyl group, a pyridazinyl group, a triazinyl group and the like.

[$R^1$, $R^2$]

In Formula (I), each of $R^1$ and $R^2$ independently represents a hydrogen atom, a substituted or unsubstituted C1-6 alkyl group, a substituted or unsubstituted C2-6 alkenyl group, a substituted or unsubstituted C2-6 alkynyl group, a hydroxyl group, a substituted or unsubstituted C1-6 alkoxy group, a formyl group, a substituted or unsubstituted C1-6 alkyl carbonyl group, a substituted or unsubstituted C1-6 alkoxy carbonyl group, a mercapto group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted aminocarbonyl group, a substituted or unsubstituted C3-8 cycloalkyl group, a substituted or unsubstituted C6-10 aryl group, a substituted or unsubstituted C6-10 aryloxy group, a substituted or unsubstituted 3- to 6-membered heterocyclyl group, a substituted or unsubstituted amino group, a halogeno group, a cyano group, or a nitrile group, with the proviso that in the case of $R^2$ being a hydrogen atom, $R^1$ is a substituted or unsubstituted C6-10 aryl group, or a substituted or unsubstituted, 3- to 6-membered, heterocyclyl group.

Examples of the "halogeno group" of $R^1$ and $R^2$ include a fluoro group, a chloro group, a bromo group, an iodo group, and the like.

The "C1-6 alkyl group" of $R^1$ and $R^2$ may be linear or branched in the case of having 3 or more carbon atoms. Examples of the alkyl group include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group, an i-hexyl group, and the like.

Specific examples of the "substituted C1-6 alkyl group" include a C1-6 haloalkyl group such as a fluoromethyl group, a chloromethyl group, a bromomethyl group, a difluoromethyl group, a dichloromethyl group, a dibromomethyl group, a trifluoromethyl group, a trichloromethyl group, a tribromomethyl group, a 1-chloroethyl group, a 2,2,2-trifluoroethyl group, a 2,2,2-trichloroethyl group, a pentafluoroethyl group, a 4-fluorobutyl group, a 4-chlorobutyl group, a 3,3,3-trifluoropropyl group, a 2,2,2-trifluoro-1-trifluoromethylethyl group, a perfluorohexyl group, a perchlorohexyl group, or a 2,4,6-trichlorohexyl group; a C1-6 alkoxy C1-6 alkyl group such as a methoxymethyl group, an ethoxymethyl group, a methoxyethyl group, an ethoxyethyl group, a methoxy-n-propyl group, an n-propoxymethyl group, an i-propoxyethyl group, an s-butoxymethyl group, or a t-butoxyethyl group; a C6-10 aryl C1-6 alkyl group such as a benzyl group, or a phenethyl group;

a C3-8 cycloalkyl C1-6 alkyl group such as a cyclopropylmethyl group, a 2-cyclopropylethyl group, a cyclopentylmethyl group, a 2-cyclohexylethyl group, or a 2-cyclooctylethyl group; and the like.

Examples of the "C2-6 alkenyl group" of $R^1$ and $R^2$ include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group, and the like.

Examples of the "substituted C2-6 alkenyl group" include a C2-6 haloalkenyl group such as a 2-chloro-1-propenyl group, or a 2-fluoro-1-butenyl group; a C1-6 alkoxy C2-6 alkenyl group such as a 2-n-butoxy-vinyl group, or a 1-ethoxy-vinyl group; and the like.

Examples of the "C2-6 alkynyl group" of $R^1$ and $R^2$ include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, a 1,1-dimethyl-2-butynyl group, and the like.

Examples of the "substituted C2-6 alkynyl group" include a C2-6 haloalkynyl group such as a 4,4-dichloro-1-butynyl group, a 4-fluoro-1-pentynyl group, or a 5-bromo-2-pentynyl group.

Examples of the "C1-6 alkoxy group" of $R^1$ and $R^2$ include a methoxy group, an ethoxy group, an n-propoxy group, an n-butoxy group, an n-pentyloxy group, an n-hexyloxy group, an i-propoxy group, an i-butoxy group, an s-butoxy group, a t-butoxy group, an i-hexyloxy group, and the like.

Specific examples of the "substituted C1-6 alkoxy group" include a C1-6 haloalkoxy group such as a chloromethoxy group, a dichloromethoxy group, a difluoromethoxy group, a trichloromethoxy group, a trifluoromethoxy group, a 1-fluroethoxy group, a 1,1-difluroethoxy group, a 2,2,2-trifluroethoxy group, a pentafluroethoxy group, or a 2,2,3,4,4,4-hexafluoro-butoxy group; a C1-6 alkoxy C1-6 alkoxy group such as a methoxymethoxy group, or a methoxyethoxy group; a C6-10 aryl C1-6 alkoxy group such as a benzyloxy group or a phenethyloxy group; a C3-8 cycloalkyl C1-6 alkoxy group such as a cyclopropylmethyloxy group; and the like.

Examples of the "C1-6 alkyl carbonyl group" of $R^1$ and $R^2$ include an acetyl group, a propionyl group, and the like.

Specific examples of the "substituted C1-6 alkyl carbonyl group" include a C1-6 haloalkyl carbonyl group such as a chloroacetyl group, a trifluoroacetyl group, or a trichloroacetyl group.

Examples of the "C1-6 alkoxycarbonyl group" of $R^1$ and $R^2$ include a methoxycarbonyl group, an ethoxycarbonyl group, an n-propoxycarbonyl group, an i-propoxycarbonyl group, a t-butoxycarbonyl group, and the like.

Specific examples of the "substituted C1-6 alkoxy carbonyl group" include a C1-6 haloalkoxy carbonyl group such as a fluoromethoxycarbonyl group, a chloromethoxycarbonyl group, a bromomethoxycarbonyl group, a difluoromethoxycarbonyl group, a dichloromethoxycarbonyl group, a dibromomethoxycarbonyl group, a trifluoromethoxycarbonyl group, a trichloromethoxycarbonyl group, a tribromomethoxycarbonyl group, or a 2,2,2-trifluoroethoxycarbonyl group; a C3-8 cycloalkyl C1-6 alkoxy carbonyl group such as a cyclopropylmethoxycarbonyl group, a cyclobutylmethoxycarbonyl group, a cyclopentylmethoxycarbonyl group, a cyclohexylmethoxycarbonyl group, or a 2-cyclopropylethoxycarbonyl group; and the like.

Examples of the "C1-6 alkylthio group" of $R^1$ and $R^2$ include a methylthio group, an ethylthio group, an n-propylthio group, an n-butylthio group, an n-pentylthio group, an n-hexylthio group, an i-propylthio group, an i-butylthio group, and the like.

Specific examples of the "substituted C1-6 alkylthio group" include a C1-6 haloalkylthio group such as a trifluoromethylthio group, or a 2,2,2-trifluoroethylthio group.

Examples of the "C1-6 alkylsulfinyl group" of $R^1$ and $R^2$ include a methylsulfinyl group, an ethylsulfinyl group, a t-butylsulfinyl group, and the like.

Specific examples of the "substituted C1-6 alkylsulfinyl group" include a C1-6 haloalkylsulfinyl group such as a trifluoromethylsulfinyl group, or a 2,2,2-trifluoroethylsulfinyl group.

Examples of the "C1-6 alkylsulfonyl group" of $R^1$ and $R^2$ include a methylsulfonyl group, an ethylsulfonyl group, a t-butylsulfonyl group, and the like.

Specific examples of the "substituted C1-6 alkylsulfonyl group" include a C1-6 haloalkylsulfonyl group such as a trifluoromethylsulfonyl group, or a 2,2,2-trifluoroethylsulfonyl group.

Examples of the preferable substituted groups on the "C1-6 alkyl group", "C2-6 alkenyl group", "C2-6 alkynyl group", "C1-6 alkoxy group", "C1-6 alkyl carbonyl group", "C1-6 alkoxy carbonyl group", "C1-6 alkylthio group", "C1-6 alkylsulfinyl group", and "C1-6 alkylsulfonyl group" of $R^1$ and $R^2$ preferably include a C1-6 alkoxy group, a halogeno group, a cyano group, a C3-8 cycloalkyl group, a C6-10 aryl group, a 3- to 6-membered heterocyclyl group, and the like.

Specific examples of the "substituted aminocarbonyl group" of $R^1$ and $R^2$ include a C1-6 alkyl aminocarbonyl group such as a methyl aminocarbonyl group, an ethyl aminocarbonyl group, a dimethyl aminocarbonyl group, or a diethyl aminocarbonyl group.

Examples of the "C3-8 cycloalkyl group" of $R^1$ and $R^2$ include a cyclopropyl group, a cyclobutyl group, a cyclopentyl group, a cyclohexyl group, a cycloheptyl group, and the like.

The "C6-10 aryl group" of $R^1$ and $R^2$ may be a monocyclic ring or a polycyclic ring. As long as the polycyclic aryl group has at least one aromatic ring, the remaining rings may be a saturated alicyclic ring, an unsaturated alicyclic ring or an aromatic ring.

Examples of the "C6-10 aryl group" include a phenyl group, a naphthyl group, an azulenyl group, an indenyl group, an indanyl group, a tetralinyl group, and the like.

Examples of the "C6-10 aryloxy group" of $R^1$ and $R^2$ include a phenoxy group, a naphthoxy group, and the like.

The "3- to 6-membered heterocyclyl group" of $R^1$ and $R^2$ is a group having 1 to 4 heteroatoms selected from the group consisting of a nitrogen atom, an oxygen atom and a sulfur atom as a constitutional atom of the ring. The heterocyclyl group may be a monocyclic one or a polycyclic one. As long as the polyheterocyclyl group includes at least one hetero ring, the remaining ring may be a saturated alicyclic ring, an unsaturated alicyclic ring or an aromatic ring. Examples of the "3- to 6-membered heterocyclyl group" include a 3- to 6-membered saturated heterocyclyl group, a 5- to 6-membered heteroaryl group, a 5- to 6-membered partially unsaturated heterocyclyl group, and the like.

Examples of the "3- to 6-membered saturated heterocyclyl group include an aziridinyl group, an epoxy group, a pyrrolidinyl group, a tetrahydrofuranyl group, a thiazolidinyl group, a piperidyl group, a piperazinyl group, a morpholinyl group, a dioxolanyl group (specifically, a [1,3]dioxolanyl group), a dioxanyl group (specifically, a [1,3]dioxanyl group, or a [1,4]dioxanyl group), and the like. A 5- to 6-membered saturated heterocyclyl group is preferable.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group (specifically, a [1,2,3]triazolyl group or a [1,2,4]triazolyl group), an oxadiazolyl group (specifically, a [1,2,4]oxadiazolyl group, or a [1,3,4]oxadiazolyl group), a thiadiazolyl group, a tetrazolyl group, and the like.

Examples of the 6-membered heteroaryl group include a pyridyl group, a pyrazinyl group, a pyrimidinyl group, a pyridazinyl group, a triazinyl group, and the like.

Examples of the partially unsaturated 5-membered heterocyclyl group include a pyrrolinyl group, an imidazolinyl group (a dihydroimidazolyl group), a pyrazolinyl group, an oxazolinyl group, an isoxazolinyl group, a thiazolinyl group, and the like, Examples of the partially unsaturated 6-membered heterocyclyl group include a thiopyranyl group, a 2H-pyridin-1-yl group, a 4H-pyridin-1-yl group, and the like.

Examples of the substituted groups on the "C3-8 cycloalkyl group", "C6-10 aryl group", "C6-10 aryloxy group", and "3- to 6-membered heterocyclyl group" of $R^1$ and $R^2$ preferably include a halogeno group such as a fluoro group, a chloro group, a bromo group, or an iodo group; a C1-6 alkyl group such as a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group, or an i-hexyl group; a C1-6 haloalkyl group such as a chloromethyl group, a chloroethyl group, a trifluoromethyl group, a difluoromethyl group, a 2,2,2-trifluoroethyl group, a perfluoroethyl group, a 1,2-dichloro-n-propyl group, a 1-fluoro-n-butyl group, or a perfluoro-n-pentyl group; a C1-6 haloalkoxy group such as a trifluoromethoxy group, a 2-chloro-n-propoxy group, or a 2,3-dichlorobutoxy group; an amino group, a mono C1-6 alkoxy carbonyl amino group such as a t-butoxycarbonyl amino group; a cyano group; and an oxo group. Examples of the substituted groups more preferably include a halogeno group such as a fluoro group, a chloro group, a bromo group, or an iodo group; a C1-6 alkyl group such as a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group, or an i-hexyl group; a C1-6 haloalkyl group such as a chloromethyl group, a chloroethyl group, a trifluoromethyl group, a difluoromethyl group, a 2,2,2-trifluoroethyl group, a perfluoroethyl group, a 1,2-dichloro-n-propyl group, a 1-fluoro-n-butyl group, or a perfluoro-n-pentyl group; a C1-6 haloalkoxy group such as a trifluoromethoxy group, a 2-chloro-n-propoxy group, or a 2,3-dichlorobutoxy group; and an amino group. Examples of the substituted groups, in particular, preferably include a fluoro group, a chloro group, a methyl group, and an amino group.

Examples of the "substituted amino group" of $R^1$ and $R^2$ include a C1-6 alkyl amino group such as a methylamino group, an n-butylamino group, a dimethylamino group, or a diethylamino group; a C3-8 cycloalkyl amino group such as a cyclopropylamino group; a C1-6 alkyl carbonylamino group such as an acetylamino group, a propanoylamino group, a butyrylamino group, or an i-propyl carbonyl amino group; a mono(C1-6 alkoxy carbonyl) amino group such as a methoxycarbonyl amino group, an ethoxycarbonyl amino group, an n-propoxycarbonyl amino group, an i-propoxycarbonyl amino group, or a t-butoxycarbonyl amino group; a di(C1-6 alkoxy carbonyl) amino group such as a di(methoxycarbonyl) amino group, a di(ethoxycarbonyl) amino group, a di(i-propoxycarbonyl) amino group, a di(n-propoxycarbonyl) amino group, or a di(t-butoxycarbonyl) amino group; and the like.

[$R^3$]

In Formula (I), $R^3$ represents a substituted or unsubstituted C1-6 alkylthio group, a substituted or unsubstituted C1-6 alkylsulfinyl group, a substituted or unsubstituted C1-6 alkylsulfonyl group, a substituted or unsubstituted C1-6 alkylsulfonyloxy group, or a group represented by —S(=O)(=N—$R^a$)—$R^b$, in which each of $R^a$ and $R^b$ independently represents a substituted or unsubstituted C1-6 alkyl group.

Examples of the "substituted or unsubstituted C1-6 alkylthio group", "substituted or unsubstituted C1-6 alkylsulfinyl group", and "substituted or unsubstituted C1-6 alkylsulfonyl group" of $R^3$ include the same examples as listed in the aforementioned $R^1$ and $R^2$.

Examples of the "C1-6 alkylsulfonyloxy group" of $R^3$ include a methylsulfonyloxy group, an ethylsulfonyloxy group, a t-butylsulfonyloxy group, and the like.

Examples of the preferable substituted groups on the "C1-6 alkylsulfonyloxy group" of $R^3$ include a C1-6 alkoxy group, a halogeno group, a cyano group, a C3-8 cycloalkyl group, a C6-10 aryl group, a 3- to 6-membered heterocyclyl group, and the like. Specific examples of the "substituted C1-6 alkyl sulfonyloxy group" include a C1-6 haloalkylsulfonyloxy group such as a trifluoromethylsulfonyloxy group, or a 2,2,2-trifluoroethylsulfonyloxy group.

As examples of the "substituted or unsubstituted C1-6 alkyl group" of $R^a$ and $R^b$ in the group represented by a formula: —S(=O)(=N—$R^a$)—$R^b$, the same examples as those listed in the aforementioned $R^1$ and $R^2$ can be mentioned.

[$R^4$, $R^5$]

In Formula (I), each of $R^4$ and $R^5$ independently represents a hydrogen atom, a halogeno group, a cyano group, a substituted or unsubstituted C1-6 alkyl group, a substituted or unsubstituted C2-6 alkenyl group, a substituted or unsubstituted C2-6 alkynyl group, a hydroxyl group, a substituted or unsubstituted C1-6 alkoxy group, a formyl group, a substituted or unsubstituted C1-6 alkyl carbonyl group, a substituted or unsubstituted C1-6 alkoxy carbonyl group, a substituted or unsubstituted C1-6 alkylthio group, a substituted or unsubstituted C1-6 alkylsulfinyl group, a substituted or unsubstituted C1-6 alkyl sulfonyl group, a substituted or unsubstituted C1-6 alkylsulfonyloxy group, a substituted or unsubstituted amino group, or a group represented by —S(=O)(=N—$R^a$)—$R^b$, in which each of $R^a$ and $R^b$ independently represents a substituted or unsubstituted C1-6 alkyl group.

As examples of the "halogeno group" of $R^4$ and $R^5$, the same examples as those listed in $R^1$ and $R^2$ can be mentioned.

As examples of the "substituted or unsubstituted C1-6 alkyl group", "substituted or unsubstituted C2-6 alkenyl group", "substituted or unsubstituted C2-6 alkynyl group", "substituted or unsubstituted C1-6 alkoxy group", "substituted or unsubstituted C1-6 alkyl carbonyl group", "substituted or unsubstituted C1-6 alkoxy carbonyl group", "substituted or unsubstituted C1-6 alkylthio group", "substituted or unsubstituted C1-6 alkylsulfinyl group", "substituted amino group", and "substituted or unsubstituted C1-6 alkylsulfonyl group" of $R^4$ and $R^5$, the same examples as those listed in the aforementioned $R^1$ and $R^2$ can be mentioned.

As examples of the "substituted or unsubstituted C1-6 alkylsulfonyloxy group" of $R^4$ and $R^5$, the same examples as those listed in the aforementioned $R^3$ can be mentioned.

As examples of the "substituted or unsubstituted C1-6 alkyl group" of $R^a$ and $R^b$ in the group represented by —S(=O)(=N—$R^a$)—$R^b$, the same examples as those listed in the aforementioned $R^1$ and $R^2$ can be mentioned.

[Ar]

In Formula (I), Ar represents a substituted or unsubstituted C6-10 aryl group or a substituted or unsubstituted 5- to 6-membered heteroaryl group.

As examples of the "C6-10 aryl group" or "5- to 6-membered heteroaryl group" of Ar, the same examples as those listed in the aforementioned $R^1$ and $R^2$ can be mentioned.

Example of the substituted groups of "C6-10 aryl group" and "5- to 6-membered heteroaryl group" of Ar preferably include a C1-6 haloalkyl group such as a chloromethyl group, a chloroethyl group, a trifluoromethyl group, a difluoromethyl group, a 2,2,2-trifluoroethyl group, a perfluoroethyl group, a 1,2-dichloro-n-propyl group, a 1-fluoro-n-butyl group, or a perfluoro-n-pentyl group; a C1-6 haloalkoxy group such as a trifluoromethoxy group, a 2-chloro-n-propoxy group, or a 2,3-dichlorobutoxy group; a C1-6 haloalkylthio group such as a trifluoromethylthio group, or a 2,2,2-trifluoroethylthio group; and a C1-6 haloalkylsulfonyl group such as a trifluoromethylsulfonyl group, or a 2,2,2-trifluoroethylsulfonyl group. Example thereof more preferably include a trifluoromethyl group, a difluoromethyl group, a perfluoroethyl group, a trifluoromethoxy group, a trifluoromethylthio group, or a trifluoromethylsulfonyl group, and in particular, preferably include a trifluoromethyl group, a perfluoroethyl group, or a trifluoromethoxy group.

Ar is preferably a substituted or unsubstituted phenyl group, or a substituted or unsubstituted 5- to 6-membered heteroaryl group, is more preferably a substituted phenyl group, a substituted pyrazolyl group, or a substituted pyridyl group, and in particular, preferably a substituted phenyl group.

In Formula (I), preferably, $R^1$ is a hydrogen atom, $R^2$ is a substituted or unsubstituted C6-10 aryl group, or a substituted or unsubstituted 3- to 6-membered heterocyclyl group (preferably a substituted or unsubstituted 5- to 6-membered heteroaryl group), $R^3$ is a C1-6 alkylsulfonyl group (preferably an ethylsulfonyl group), $R^4$ is a C1-6 alkyl group (preferably a methyl group), or a substituted or unsubstituted amino group (preferably an amino group), and $R^5$ is a hydrogen atom.

In Formula (I), preferably, $R^1$ is a hydrogen atom, $R^2$ is a substituted or unsubstituted 5- to 6-membered heteroaryl group, $R^3$ is a C1-6 alkylsulfonyl group (preferably an ethylsulfonyl group), $R^4$ is a C1-6 alkyl group (preferably a methyl group), and $R^5$ is a hydrogen atom.

In Formula (I), preferably, $R^1$ is a hydrogen atom, $R^2$ is a substituted or unsubstituted 5- to 6-membered heteroaryl group, $R^3$ is a C1-6 alkylsulfonyl group (preferably an ethylsulfonyl group), $R^4$ is a substituted or unsubstituted amino group (preferably an amino group), and $R^5$ is a hydrogen atom.

In Formula (I), preferably, $R^1$ is a substituted or unsubstituted C6-10 aryl group (preferably a halogeno group-substituted phenyl group), or a substituted or unsubstituted 3- to 6-membered heterocyclyl group (preferably a substituted or unsubstituted 5- to 6-membered heteroaryl group), $R^2$ is a hydrogen atom, $R^3$ is a C1-6 alkylsulfonyl group (preferably an ethylsulfonyl group), $R^4$ is a C1-6 alkyl group (preferably a methyl group), or a substituted or unsubstituted amino group (preferably an amino group), and $R^5$ is a hydrogen atom.

In Formula (I), preferably, $R^1$ is a substituted phenyl group (preferably a halogeno group-substituted phenyl group), or a 6-membered heteroaryl group, $R^2$ is a hydrogen atom, $R^3$ is a C1-6 alkylsulfonyl group (preferably an ethylsulfonyl group), $R^4$ is a C1-6 alkyl group (preferably a methyl group), and $R^5$ is a hydrogen atom.

In Formula (I), preferably, $R^1$ is a substituted phenyl group (preferably a halogeno group-substituted phenyl group), or a 5- to 6-membered heteroaryl group, $R^2$ is a hydrogen atom, $R^3$ is a C1-6 alkylsulfonyl group (preferably an ethylsulfonyl group), $R^4$ is a substituted or unsubstituted amino group (preferably an amino group), and $R^5$ is a hydrogen atom.

A salt of compound (I) is not particularly limited as long as the salt is an agriculturally and horticulturally acceptable salt. Examples of the salt of compound (I) include a salt of an inorganic acid such as hydrochloric acid, or sulfuric acid; a salt of an organic acid such as acetic acid, or lactic acid; a salt of an alkaline metal such as lithium, sodium, or potassium; a salt of an alkaline earth metal such as calcium, or magnesium; a salt of a transition metal such as iron, or copper; a salt of an organic base such as ammonia, triethylamine, tributylamine, pyridine, or hydrazine; and the like.

The compound (I) or a salt thereof is not particularly limited by the preparation method thereof. For example, the compound (I) or the salt thereof may be obtained by means of the well-known preparation method described in the working examples, and the like. In addition, the salt of the compound of formula (I) may be produced from the compound of formula (I) by means of a well-known method.

The diaryl pyrazole compound of the present invention has a superior effect for controlling harmful organisms such as various agricultural pests affecting the plant growth, and acari.

In addition, the diaryl pyrazole compound of the present invention has a reduced phytotoxicity against plants and has a low level of toxicity against fish or warm-blooded animals, and for this reason, the diaryl pyrazole compound of the present invention is a compound with high safety. For this reason, the compound of the present invention is useful as an active ingredient of a pesticide or an acaricide.

In addition, in recent years, many pests such as diamondback moths, planthoppers, leafhoppers and aphids have developed a resistance to various types of conventional agrochemicals, and for this reason, a problem occurs in which the efficacy of the conventional agrochemicals has become insufficient. Therefore, agrochemicals that are effective even for the resistant strains of pests are desired. The diaryl pyrazole compounds of the present invention exhibit superior effects for controlling not only the sensitive strains of pests, but also various resistant strains of pests and acaricide-resistant strains of acari.

The diaryl pyrazole compounds of the present invention have a superior effect for controlling the ectoparasites and endoparasites harmful for humans and animals. In addition, the diaryl pyrazole compounds of the present invention have a low level of toxicity to the fish or warm-blooded animals, and for this reason, the diaryl pyrazole compounds are highly safe compounds. For this reason, the diaryl pyrazole compounds of the present invention are useful as an active ingredient of a formulation for controlling ectoparasites and endoparasites.

In addition, the diaryl pyrazole compounds of the present invention are effective for controlling the targeted organisms in any development stages, and exhibit superior effects of controlling, for example, acari and insects in the stages of eggs, nymph, larvae, pupae and adults.

[Formulation for Controlling Harmful Organisms, Insecticide, or Acaricide]

The formulation for controlling harmful organisms, the insecticide, or the acaricide of the present invention contains at least one compound selected from the diaryl pyrazole compounds of the present invention as an active ingredient. The amount of the diaryl pyrazole compound contained in the formulation for controlling harmful organisms, the insecticide, or the acaricide of the present invention is not particularly limited as long as an effect of controlling harmful organisms is exhibited.

The formulation for controlling harmful organisms, the insecticide, or the acaricide of the present invention is preferably used for crops; green stuff; edible roots; tuber crops; flowers; fruit trees; trees of tea, coffee, cacao or foliage plants; grasses for pastures; grasses for lawns; plants such as cotton; or the like.

As for the application to the plants, the formulation for controlling harmful organisms, the insecticide or the acaricide of the present invention may be applied on any one part of the plants, such as leaf, stem, stalk, flower, bud, fruit, seed, sprout, root, tuber, tuberous root, shoot, cutting and the like.

In addition, the plant varieties for which the formulation for controlling harmful organisms, the insecticide or the acaricide of the present invention is applicable are not particularly limited. Examples of the plant varieties include the originals, varieties, improved varieties, cultivated varieties, mutant plants, hybrid plants, genetically modified organisms (GMO) and the like.

The formulations for controlling harmful organisms of the present invention can be used for controlling various agricultural pests and acari by seed treatment, foliar spraying, soil application or water surface application and the like.

Specific examples of the various agricultural pests and acari which can be controlled by the formulations for controlling harmful organisms of the present invention are shown below.

(1) Lepidoptera Butterflies and Moths (a) Arctiidae moths, for example, *Hyphantria cunea* and *Lemyra imparilis*;

(b) Bucculatricidae moths, for example, *Bucculatrix pyrivorella*;

(c) Carposinidae, for example, *Carposina sasakii*;

(d) Crambidae moths, for example, *Diaphania indica* and *Diaphania nitidalis* of *Diaphania* spp.; *Ostrinia furnacalis*, *Ostrinia nubilalis* and *Ostrinia scapulalis* of *Ostrinia* spp.; and others such as *Chilo suppressalis*, *Cnaphalocrocis medinalis*, *Conogethes punctiferalis*, *Diatraea grandiosella*, *Glyphodes pyloalis*, *Hellula undalis* and *Parapediasia teterrella*;

(e) Gelechiidae moths, for example, *Helcystogramma triannulella*, *Pectinophora gossypiella*, *Phthorimaea operculella* and *Sitotroga cerealella*;

(f) Geometridae moths, for example, *Ascotis selenaria*;

(g) Gracillariidae moths, for example, *Caloptilia theivora*, *Phyllocnistis citrella* and *Phyllonorycter ringoniella*;

(h) Hesperiidae butterflies, for example, *Parnara guttata*;

(i) Lasiocampidae moths, for example, *Malacosoma neustria*;

(j) Lymantriidae moths, for example, *Lymantria dispar* and *Lymantria monacha* of *Lymantria* spp.; and others such as *Euproctis pseudoconspersa* and *Orgyia thyellina*;

(k) Lyonetiidae moths, for example, *Lyonetia clerkella* and *Lyonetia prunifoliella malinella* of *Lyonetia* spp.;

(l) Noctuidae moths, for example, *Spodoptera depravata*, *Spodoptera eridania*, *Spodoptera exigua*, *Spodoptera frugiperda*, *Spodoptera littoralis* and *Spodoptera litura* of *Spodoptera* spp.; *Autographa gamma* and *Autographa nigrisigna* of *Autographa* spp.; *Agrotis ipsilon* and *Agrotis segetum* of *Agrotis* spp.; *Helicoverpa armigera*, *Helicoverpa assulta* and *Helicoverpa zea* of *Helicoverpa* spp.; *Heliothis armigera* and *Heliothis virescens* of *Heliothis* spp.; and others such as *Aedia leucomelas*, *Ctenoplusia agnata*, *Eudocima tyrannus*, *Mamestra brassicae*, *Mythimna separata*, *Naranga aenescens*, *Panolis japonica*, *Peridroma saucia*, *Pseudoplusia includens* and *Trichoplusia ni*;

(m) Nolidae moths, for example, *Earias insulana*;

(n) Pieridae butterflies, for example, *Pieris brassicae* and *Pieris rapae crucivora* of *Pieris* spp.;

(o) Plutellidae moths, for example, *Acrolepiopsis sapporensis* and *Acrolepiopsis suzukiella* of *Acrolepiopsis* spp.; and others such as *Plutella xylostella*;

(p) Pyralidae moths, for example, *Cadra cautella*, *Elasmopalpus lignosellus*, *Etiella zinckenella* and *Galleria mellonella*;

(q) Sphingidae moths, for example, *Manduca quinquemaculata* and *Manduca sexta* of *Manduca* spp.;

(r) Stathmopodidae moths, for example, *Stathmopoda masinissa*;

(s) Tineidae moths, for example, *Tinea translucens*;

(t) Tortricidae moths, for example, *Adoxophyes honmai* and *Adoxophyes orana* of *Adoxophyes* spp.; *Archips breviplicanus* and *Archips fuscocupreanus* of *Archips* spp.; and others such as *Choristoneura fumiferana*, *Cydia pomonella*, *Eupoecilia ambiguella*, *Grapholitha molesta*, *Homona magnanima*, *Leguminivora glycinivorella*, *Lobesia botrana*, *Matsumuraeses phaseoli*, *Pandemis heparana* and *Sparganothis pilleriana*; and (u) Yponomeutidae moths, for example, *Argyresthia conjugella*.

(2) Thysanoptera Insect Pests (a) Phlaeothripidae, for example, *Ponticulothrips diospyrosi*; and (b) Thripidae, for example, *Frankliniella intonsa* and *Frankliniella occidentalis* of *Frankliniella* spp.; *Thrips palmi* and *Thrips tabaci* of *Thrips* spp.; and others such as *Heliothrips haemorrhoidalis* and *Scirtothrips dorsalis*.

(3) Hemiptera Insect Pests (A) Archaeorrhyncha (a) Delphacidae, for example, *Laodelphax striatella*, *Nilaparvata lugens*, *Perkinsiella saccharicida* and *Sogatella furcifera*.

(B) Clypeorrhyncha (a) Cicadellidae, for example, *Empoasca fabae*, *Empoasca nipponica*, *Empoasca onukii* and *Empoasca sakaii* of *Empoasca* spp.; and others such as *Arboridia apicalis*, *Balclutha saltuella*, *Epiacanthus stramineus*, *Macrosteles striifrons* and *Nephotettix cincticeps*.

(C) Heteroptera (a) Alydidae, for example, *Riptortus clavatus*;

(b) Coreidae, for example, *Cletus punctiger* and *Leptocorisa chinensis*;

(c) Lygaeidae, for example, *Blissus leucopterus*, *Cavelerius saccharivorus* and *Togo hemipterus*;

(d) Miridae, for example, *Halticus insularis*, *Lygus lineolaris*, *Psuedatomoscelis seriatus*, *Stenodema sibiricum*, *Stenotus rubrovittatus* and *Trigonotylus caelestialium*;

(e) Pentatomidae, for example, *Nezara antennata* and *Nezara viridula* of *Nezara* spp.; *Eysarcoris aeneus*, *Eysarcoris lewisi* and *Eysarcoris ventralis* of *Eysarcoris* spp.; and others such as *Dolycoris baccarum*, *Eurydema rugosum*, *Glaucias subpunctatus*, *Halyomorpha halys*, *Piezodorus hybneri*, *Plautia crossota* and *Scotinophora lurida*;

(f) Pyrrhocoridae, for example, *Dysdercus cingulatus*;

(g) Rhopalidae, for example, *Rhopalus msculatus*;

(h) Scutelleridae, for example, *Eurygaster integriceps*; and (i) Tingidae, for example, *Stephanitis nashi*.

(D) Sternorrhyncha (a) Adelgidae, for example, *Adelges laricis*;

(b) Aleyrodidae, for example, *Bemisia argentifolii* and *Bemisia tabaci* of *Bemisia* spp.; and others such as *Aleurocanthus spiniferus*, *Dialeurodes citri* and *Trialeurodes vaporariorum*;

(c) Aphididae, for example, *Aphis craccivora*, *Aphis fabae*, *Aphis forbesi*, *Aphis gossypii*, *Aphis pomi*, *Aphis sambuci* and *Aphis spiraecola* of *Aphis* spp.; *Rhopalosiphum maidis* and *Rhopalosiphum padi* of *Rhopalosiphum* spp.; *Dysaphis plantaginea* and *Dysaphis radicola* of *Dysaphis* spp.; *Macrosiphum avenae* and *Macrosiphum euphorbiae* of *Macrosiphum* spp.; *Myzus cerasi*, *Myzus persicae* and *Myzus varians* of *Myzus* spp.; and others such as *Acyrtho-*

*siphon pisum, Aulacorthum solani, Brachycaudus helichrysi, Brevicoryne brassicae, Chaetosiphon fragaefolii, Hyalopterus pruni, Hyperomyzus lactucae, Lipaphis erysimi, Megoura viciae, Metopolophium dirhodum, Nasonovia ribis-nigri, Phorodon humuli, Schizaphis graminum, Sitobion avenae* and *Toxoptera aurantii;*

(d) Coccidae, for example, *Ceroplastes ceriferus* and *Ceroplastes rubens* of *Ceroplastes* spp.;

(e) Diaspididae, for example, *Pseudaulacaspis pentagona* and *Pseudaulacaspis prunicola* of *Pseudaulacaspis* spp.; *Unaspis euonymi* and *Unaspis yanonensis* of *Unaspis* spp.; and others such as *Aonidiella aurantii, Comstockaspis perniciosa, Fiorinia theae* and *Pseudaonidia paeoniae;*

(f) Margarodidae, for example, *Drosicha corpulenta* and *Icerya purchasi;*

(g) Phylloxeridae, for example, *Viteus vitifolii;*

(h) Pseudococcidae, for example, *Planococcus citri* and *Planococcus kuraunhiae* of *Planococcus* spp.; and others such as *Phenacoccus solani* and *Pseudococcus comstocki;* and (i) Psyllidae, for example, *Psylla mali* and *Psylla pyrisuga* of *Psylla* spp.; and others such as *Diaphorina citri.*

(4) *Polyphaga* Insect Pests (a) Anobiidae, for example, *Lasioderma serricorne;*

(b) Attelabidae, for example, *Byctiscus betulae* and *Rhynchites heros;*

(c) Bostrichidae, for example, *Lyctus brunneus;*

(d) Brentidae, for example, *Cylas formicarius;*

(e) Buprestidae, for example, *Agrilus sinuatus;*

(f) Cerambycidae, for example, *Anoplophora malasiaca, Monochamus alternatus, Psacothea hilaris* and *Xylotrechus pyrrhoderus;*

(g) Chrysomelidae, for example, *Bruchus pisorum* and *Bruchus rufimanus* of *Bruchus* spp.; *Diabrotica barberi, Diabrotica undecimpunctata* and *Diabrotica virgifera* of *Diabrotica* spp.; *Phyllotreta nemorum* and *Phyllotreta striolata* of *Phyllotreta* spp.; and others such as *Aulacophora femoralis, Callosobruchus chinensis, Cassida nebulosa, Chaetocnema concinna, Leptinotarsa decemlineata, Oulema oryzae* and *Psylliodes angusticollis;*

(h) Coccinellidae, for example, *Epilachna varivestis* and *Epilachna vigintioctopunctata* of *Epilachna* spp.;

(i) Curculionidae, for example, *Anthonomus grandis* and *Anthonomus pomorum* of *Anthonomus* spp.; *Sitophilus granarius* and *Sitophilus zeamais* of *Sitophilus* spp.; and others such as *Echinocnemus squameus, Euscepes postfasciatus, Hylobius abietis, Hypera postica, Lissohoptrus oryzophilus, Otiorhynchus sulcatus, Sitona lineatus* and *Sphenophorus venatus;*

(j) Elateridae, for example, *Melanotus fortnumi* and *Melanotus tamsuyensis* of *Melanotus* spp.;

(k) Nitidulidae, for example, *Epuraea domina;*

(l) Scarabaeidae, for example, *Anomala cuprea* and *Anomala rufocuprea* of *Anomala* spp.; and others such as *Cetonia aurata, Gametis jucunda, Heptophylla picea, Melolontha* and *Popillia japonica;*

(m) Scolytidae, for example, *Ips typographus;*

(n) Staphylinidae, for example, *Paederus fuscipes;*

(o) Tenebrionidae, for example, *Tenebrio molitor* and *Tribolium castaneum;* and (p) Trogossitidae, for example, *Tenebroides mauritanicus.*

(5) Diptera Insect Pests (A) Brachycera (a) Agromyzidae, for example, *Liriomyza bryoniae, Liriomyza chinensis, Liriomyza sativae* and *Liriomyza trifolii* of *Liriomyza* spp.; and others such as *Chromatomyia horticola* and *Agromyza oryzae;*

(b) Anthomyiidae, for example, *Delia platura* and *Delia radicum* of *Delia* spp.; and others such as *Pegomya cunicularia;*

(c) Drosophilidae, for example, *Drosophila melanogaster* and *Drosophila suzukii* of *Drosophila* spp.;

(d) Ephydridae, for example, *Hydrellia griseola;*

(e) Psilidae, for example, *Psila rosae;* and (f) Tephritidae, for example, *Bactrocera cucurbitae* and *Bactrocera dorsalis* of *Bactrocera* spp.; *Rhagoletis cerasi* and *Rhagoletis pomonella* of *Rhagoletis* spp.; and others such as *Ceratitis capitata* and *Dacus oleae.*

(B) Nematocera (a) Cecidomyiidae, for example, *Asphondylia yushimai, Contarinia sorghicola, Mayetiola destructor* and *Sitodiplosis mosellana.*

(6) Orthoptera Insect Pests (a) Acrididae, for example, *Schistocerca americana* and *Schistocerca gregaria* of *Schistocerca* spp.; and others such as *Chortoicetes terminifera, Dociostaurus maroccanus, Locusta migratoria, Locustana pardalina, Nomadacris septemfasciata* and *Oxya yezoensis;*

(b) Gryllidae, for example, *Acheta domestica* and *Teleogryllus emma;*

(c) Gryllotalpidae, for example, *Gryllotalpa orientalis;* and (d) Tettigoniidae, for example, *Tachycines asynamorus.*

(7) Acari (A) Acaridida of Astigmata (a) Acaridae mites, for example, *Rhizoglyphus echinopus* and *Rhizoglyphus robini* of *Rhizoglyphus* spp.; *Tyrophagus neiswanderi, Tyrophagus perniciosus, Tyrophagus putrescentiae* and *Tyrophagus similis* of *Tyrophagus* spp.; and others such as *Acarus siro, Aleuroglyphus ovatus* and *Mycetoglyphus fungivorus;*

(B) Actinedida of Prostigmata (a) Tetranychidae mites, for example, *Bryobia praetiosa* and *Bryobia rubrioculus* of *Bryobia* spp.; *Eotetranychus asiaticus, Eotetranychus boreus, Eotetranychus celtis, Eotetranychus geniculatus, Eotetranychus kankitus, Eotetranychus pruni, Eotetranychus shii, Eotetranychus smithi, Eotetranychus suginamensis* and *Eotetranychus uncatus* of *Eotetranychus* spp.; *Oligonychus hondoensis, Oligonychus ilicis, Oligonychus karamatus, Oligonychus mangiferus, Oligonychus orthius, Oligonychus perseae, Oligonychus pustulosus, Oligonychus shinkajii* and *Oligonychus ununguis* of *Oligonychus* spp.; *Panonychus citri, Panonychus mori* and *Panonychus ulmi* of *Panonychus* spp.; *Tetranychus cinnabarinus, Tetranychus kanzawai, Tetranychus ludeni, Tetranychus quercivorus, Tetranychus phaselus, Tetranychus urticae* and *Tetranychus viennensis* of *Tetranychus* spp.; *Aponychus corpuzae* and *Aponychus firmianae* of *Aponychus* spp.; *Sasanychus akitanus* and *Sasanychus pusillus* of *Sasanychus* spp.; *Shizotetranychus celarius, Shizotetranychus longus, Shizotetranychus miscanthi, Shizotetranychus recki* and *Shizotetranychus schizopus* of *Shizotetranychus* spp.; and others such as *Tetranychina harti, Tuckerella pavoniformis* and *Yezonychus sapporensis;*

(b) Tenuipalpidae mites, for example, *Brevipalpus lewisi, Brevipalpus obovatus, Brevipalpus phoenicis, Brevipalpus russulus* and *Brevipalpus californicus* of *Brevipalpus* spp.; *Tenuipalpus pacificus* and *Tenuipalpus zhizhilashviliae* of *Tenuipalpus* spp.; and others such as *Dolichotetranychus floridanus;*

(c) Eriophyidae mites, for example, *Aceria diospyri, Aceria ficus, Aceria japonica, Aceria kuko, Aceria paradianthi, Aceria tiyingi, Aceria tulipae* and *Aceria zoysiea* of *Aceria* spp.; *Eriophyes chibaensis* and *Eriophyes emarginatae* of

*Eriophyes* spp.; *Aculops lycopersici* and *Aculops pelekassi* of *Aculops* spp.; *Aculus fockeui* and *Aculus schlechtendali* of *Aculus* spp.; and others such as *Acaphylla theavagrans, Calacarus carinatus, Colomerus vitis, Calepitrimerus vitis, Epitrimerus pyri, Paraphytoptus kikus, Paracalacarus podocarpi* and *Phyllocotruta citri;*

(d) Tarsonemidae mites, for example, *Tarsonemus bilobatus* and *Tarsonemus waitei* of *Tarsonemus* spp.; and others such as *Phytonemus pallidus* and *Polyphagotarsonemus latus*; and (e) Penthaleidae mites, for example, *Penthaleus erythrocephalus* and *Penthaleus major* of *Penthaleus* spp.

The formulation for controlling harmful organisms of the present invention may be mixed or used in combination with other active constituents such as fungicides, insecticides/acaricides, nematicides and soil pesticides; and/or plant regulators, herbicides, synergists, fertilizers, soil conditioners and animal feed.

Combinations of the compound of the present invention with other active constituents can be expected to provide synergistic effects in terms of insecticidal/acaricidal/nematicidal activity. The synergistic effect can be confirmed in accordance with a conventional method by means of an equation defined by Colby (Colby. S. R.; Calculating Synergistic and Antagonistic Responses of Herbicide Combinations; Weeds, 15, pages 20-22, 1967).

Examples of the insecticides/acaricides, nematocides, soil pesticides, vermicides and the like which can be mixed or used together with the formulation for controlling harmful organisms according to the present invention are described below.

(1) Acetylcholine esterase inhibitor:

(a) Carbamate-based agents: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylylcarb, fenothiocarb, MIPC, MPMC, MTMC, aldoxycarb, allyxycarb, aminocarb, bufencarb, cloethocarb, metam-sodium, and promecarb; and (b) Organic phosphorus-based agents: acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion; bromophos-ethyl, BRP, carbophenothion, cyanofenphos, CYAP, demeton-S-methyl sulfone, dialifos, dichlofenthion, dioxabenzofos, etrimfos, fensulfothion, flupyrazofos, fonofos, formothion, fosmethilan, isazofos, jodfenphos, methacrifos, pirimiphos-ethyl, phosphocarb, propaphos, prothoate, and sulprofos.

(2) GABA-gated chloride ion channel antagonists: acetoprole, chlordane, endosulfan, ethiprole, fipronil, pyrafluprole, pyriprole, camphechlor, heptachlor, and dienochlor.

(3) Sodium channel modulators: acrinathrin, d-cis-trans-allethrin, d-trans allethrin, bifenthrin, bioallethrin, bioallethrin S-cyclopentyl isomer, bioresmethrin, cycloprothrin, cyfluthrin, β-cyfluthrin, cyhalothrin, λ-cyhalothrin, γ-cyhalothrin, cypermethrin, α-cypermethrin, β-cypermethrin, θ-cypermethrin, ξ-cypermethrin, cyphenothrin [(1R)-trans isomer], δ-methrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrum, resmethrin, silafluofen, tefluthrin, tetramethrin [(1R)-isomer], tralomethrin, transfluthrin; allethrin, pyrethrins, pyrethrin I, pyrethrin II, profluthrin, dimefluthrin, bioethanomethrin, biopermethrin, transpermethirn, fenfluthrin, fenpirithrin, flubrocythrinate, flufenprox, metofluthrin, protrifenbute, pyresmethrin, and terallethrin.

(4) Nicotinic acetylcholine receptor agonists: acetamiprid, clothianidin, dinotefuran, imidacloprid, nitenpyram, nithiazine, thiacloprid, thiamethoxam, sulfoxafl or, nicotine, and flupyradifurone.

(5) Nicotinic acetylcholine receptor allosteric modulators: spinetoram, and spinosad.

(6) Chloride channel activators: abamectin, emamectin-benzoate, lepimectin, milbemectin, ivermectin, selamectin, doramectin, eprinomectin, moxidectin, milbemycin; milbemycin oxime, and nemadectin.

(7) Juvenile hormone-like substances: hydroprene, kinoprene, methoprene, fenoxycarb, pyriproxyfen, diofenolan, epofenonane, and triprene.

(8) Other nonspecific inhibitors: methyl bromide, chloropicrin, sulfuryl fluoride, borax, and tartar emetic.

(9) Homoptera selective antifeedants: flonicamid, pymetrozine, and pyrifluquinazon.

(10) Acari growth inhibitors: clofentezine, diflovidazin, hexythiazox, and etoxazole.

(11) Microorganism-derived insect midgut inner membrane disrupting agents: *Bacillus thuringiensis* subsp. *Israelensis, Bacillus sphaericus, Bacillus thuringiensis* subsp. *Aizawai, Bacillus thuringiensis* subsp. Kurstaki, *Bacillus thuringiensis* subsp. *Tenebrionis*, Bt crop protein: Cry1Ab, Cry1Ac, Cry1Fa, Cry1A. 105, Cry2Ab, Vip3A, mCry3A, Cry3Ab, Cry3Bb, and Cry34Ab1/Cry35Ab1.

(12) Mitochondria ATP biosynthesis enzyme inhibitors: diafenthiuron, azocyclotin, cyhexatin, fenbutatin oxide, propargite, and tetradifon.

(13) Oxidative phosphorylation decouplers: chlorfenapyr, sulfluramid, DNOC; binapacryl, dinobuton, and dinocap.

(14) Nicotinic acetylcholine receptor channel blockers: bensultap, cartap hydrochloride; nereistoxin; thiosultap-sodium, and thiocyclam.

(15) Chitin synthesis inhibitors: bistrifluron, chlorfluazuron, diflubenzuron, flucycloxuron, flufenoxuron, hexaflumuron, lufenuron, novaluron, noviflumuron, teflubenzuron, triflumuron, buprofezin, and fluazuron.

(16) Diptera molting disruptors: cyromazine.

(17) Molting hormone receptor agonists: chromafenozide, halofenozide, methoxyfenozide, and tebufenozide.

(18) Octopamine receptor agonists: amitraz, demiditraz, and chlordimeform.

(19) Mitochondria electron transfer chain complex III inhibitors: acequinocyl, fluacrypyrim, and hydramethylnon.

(20) Mitochondria electron transfer chain complex I inhibitors: fenazaquin, fenpyroximate, pyrimidifen, pyridaben, tebufenpyrad, tolfenpyrad, and rotenone.

(21) Voltage-dependent sodium channel blockers: indoxacarb, and metaflumizone.

(22) Acetyl CoA carboxylase inhibitors: spirodiclofen, spiromesifen, and spirotetramat.

(23) Mitochondria electron transfer chain complex IV inhibitors: aluminum phosphide, calcium phosphide, phosphine, zinc phosphide, and cyanide.

(24) Mitochondria electron transfer chain complex II inhibitors: cyenopyrafen, cyflumetofen, and pyflubumide.

(25) Ryanodine receptor modulators: chlorantraniliprole, cyantraniliprole, flubendiamide, cyclaniliprole, and tetraniliprole.

(26) Mixed function oxidase inhibitor compounds: piperonyl butoxide.

(27) Latrophilin receptor agonists: depsipeptide, cyclodepsipeptide, 24 membered cyclodepsipeptide, and emodepside.

(28) Others (action mechanism is unknown): azadirachtin, benzoximate, bifenazate, bromopropylate, quinomethionate, cryolite, dicofol, pyridalyl, benclothiaz, sulfur, amidoflumet, 1,3-dichloropropene, DCIP, phenisobromolate, benzomate, metaldehyde, chlorobenzilate, chlothiazoben, dicyclanil, fenoxacrim, fentrifanil, flubenzimine, fluphenazine, gossyplure, japonilure, metoxadiazone, oil, potassium oleate, tetrasul; triarathene, afidopyropen, flometoquin, flufiprole, fluensulfone, meperfluthrin, tetramethylfluthrin, tralopyril, dimefluthrin, methylneodecanamide; fluralaner, afoxolaner, and fluxametamide, 5-[5-(3,5-dichlorophenyl)-5-trifluoromethyl-4,5-dihydroisoxazol-3-yl]-2-(1H-1,2,4-triazol-1-yl) benzonitrile (CAS: 943137-49-3), broflanilide, other metadiamides, *Steinernema carpocapsae*, *Steinernema glaseri*, *Pasteuria penetrans*, *Paecilomyces tenuipes*, *Paecilomyces fumosoroseus*, *Beauveria bassiana*, *Beauveria brongniartii*, *Metarhizium anisopliae*, and *Verticillium lecanii*.

(29) Parasiticide:

(a) Benzimidazole-based agents: fenbendazole, albendazole, triclabendazole, oxibendazole, mebendazole, oxfendazole, parbendazole, flubendazole, febantel, netobimin, thiophanate; thiabendazole, and cambendazole;

(b) Salicylanilide-based agents: closantel, oxyclozanide, rafoxanide, and niclosamide;

(c) Substituted phenol-based agents: nitroxinil, and nitroscanate;

(d) Pyrimidine-based agents: pyrantel, and morantel;

(e) Imidazothiazole-based agents: levamisole, and tetramisole;

(f) Tetrahydropyrimidine-based agents: praziquantel, and epsiprantel; and (g) Other antiparasitic agents: cyclodien, ryania, clorsulon, metronidazole, demiditraz, piperazine, diethylcarbamazine, dichlorophen, monepantel, tribendimidine, amidantel, thiacetarsamide, melarsomine, and arsenamide.

Specific examples of the fungicides which can be mixed or used together with the formulation for controlling harmful organisms according to the present invention are described below.

(1) Nucleic acid biosynthesis inhibitors:

(a) RNA polymerase I inhibitors: benalaxyl, benalaxyl-M, furalaxyl, metalaxyl, metalaxyl-M, oxadixyl; clozylacon, and ofurace;

(b) Adenosine deaminase inhibitors: bupirimate, dimethirimol, and ethirimol;

(c) DNA/RNA synthesis inhibitors: hymexazol, and octhilinone; and (d) DNA topoisomerase II inhibitors: oxolinic acid.

(2) Karyokinesis inhibitor and cell division inhibitors:

(a) β-Tubulin polymerization inhibitors: benomyl, carbendazim, chlorfenazole, fuberidazole, thiabendazole, thiophanate, thiophanate-methyl, diethofencarb, zoxamide, and ethaboxam;

(b) Cell division inhibitors: pencycuron; and (c) Delocalization inhibitors of spectrin-like protein: fluopicolide.

(3) Respiration inhibitors:

(a) Complex I NADH oxidoreductase inhibitors: diflumetorim and tolfenpyrad;

(b) Complex II succinic acid dehydrogenase inhibitors: benodanil, flutolanil, mepronil, isofetamid, fluopyram; fenfuram, furmecyclox, carboxin, oxycarboxin, thifluzamide, benzovindiflupyr, bixafen, fluxapyroxad, furametpyr, isopyrazam, penflufen, penthiopyrad, sedaxane, boscalid, and pyraziflumid;

(c) Complex III ubiquinol oxidase Qo inhibitors: azoxystrobin, coumoxystrobin, coumethoxystrobin, enoxastrobin, flufenoxystrobin, picoxystrobin, pyraoxystrobin, pyraclostrobin, pyrametostrobin, triclopyricarb, kresoxim-methyl, trifloxystrobin, dimoxystrobin, fenaminstrobin, metominostrobin, orysastrobin, famoxadone; fluoxastrobin, fenamidone, pyribencarb, and mandestrobin;

(d) Complex III ubiquinol reductase Qi inhibitors: cyazofamid and amisulbrom;

(e) Oxidative phosphorylation uncoupling agents: binapacryl, meptyldinocap, dinocap, fluazinam, and ferimzone;

(f) Oxidative phosphorylation inhibitors (ATP synthase inhibitors): fentin acetate, fentin chloride, and fentin hydroxide;

(g) ATP production inhibitors: silthiofam; and (h) Complex III: cytochrome bcl (ubiquinone reductase) Qx (unknown) inhibitors: ametoctradin.

(4) Amino acid and protein synthesis inhibitors:

(a) Methionine biosynthesis inhibitors: andoprim, cyprodinil, mepanipyrim, and pyrimethanil; and (b) Protein synthesis inhibitors: blasticidin S; kasugamycin, kasugamycin hydrochloride, streptomycin, and oxytetracycline.

(5) Signal transduction inhibitors:

(a) Signal transduction inhibitors: quinoxyfen and proquinazid; and (b) MAP/histidine kinase inhibitors in osmotic pressure signal transduction: fenpiclonil, fludioxonil, chlozolinate, iprodione, procymidone, and vinclozolin.

(6) Lipid and cell membrane synthesis inhibitors:

(a) Phospholipid biosynthesis and methyltransferase inhibitors: edifenphos, iprobenfos, pyrazophos, and isoprothiolane;

(b) Lipid peroxidation agents: biphenyl, chloroneb, dichloran, quintozene, tecnazene, tolclofos-methyl, and etridiazole;

(c) Agents that act upon cell membranes: iodocarb, propamocarb, propamocarb-hydrochloride, propamocarb-fosetylate, and prothiocarb;

(d) Microorganisms that disturb pathogen cell membranes: *Bacillus subtilis*, *Bacillus subtilis* strain QST713, *Bacillus subtilis* strain FZB24, *Bacillus subtilis* strain MBI600, *Bacillus subtilis* strain D747, and *Bacillus amyloliquefaciens*; and (e) Agents that disturb cell membranes: *Melaleuca alternifolia* (tea tree) extract.

(7) Cell membrane sterol biosynthesis inhibitors:

(a) C14-position demethylation inhibitors in sterol biosynthesis: triforine, pyrifenox, pyrisoxazole, fenarimol, flurprimidol, nuarimol, imazalil, imazalil-sulfate, oxpoconazole, pefurazoate, prochloraz, triflumizole, viniconazole, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, fluquinconazole, simeconazole, tebuconazole, tetraconazole, triadimefon, triadimenol, triticonazole, prothioconazole, voriconazole, and mefentrifluconazole;

(b) Δ14 reductase and Δ8→Δ7-isomerase inhibitors in sterol biosynthesis: aldimorph, dodemorph, dodemorph acetate, fenpropimorph, tridemorph, fenpropidine, piperalin, and spiroxamine;

(c) 3-keto reductase inhibitors in C4-position demethylation in sterol biosynthesis systems: fenhexamid and fenpyrazamine; and (d) Squalene epoxidase inhibitors in sterol biosynthesis systems: pyributicarb, naftifene, and terbinafine.

(8) Cell wall synthesis inhibitors:

(a) Trehalase inhibitors: validamycin;

(b) Chitin synthase inhibitors: polyoxins and polyoxorim; and (c) Cellulose synthase inhibitors: dimethomorph, flumorph, pyrimorph; benthiavalicarb isopropyl, iprovalicarb, tolprocarb, valifenalate, and mandipropamide.

(9) Melanin biosynthesis inhibitors:

(a) Reductase inhibitors in melanin biosynthesis: fthalide, pyroquilon, and tricyclazole; and (b) Anhydrase inhibitors in melanin biosynthesis: carpropamid, diclocymet, and fenoxanil.

(10) Host plant resistance-inducing agents:

(a) Agent that acts on salicylic acid biosynthetic pathway: acibenzolar-S-methyl; and (b) Others: probenazole; tiadinil; isotianil; laminarin; and *Reynoutria sachalinensis* extract.

(11) Agents for which the mode of activity is unclear: cymoxanil, fosetyl-aluminum, phosphoric acid (phosphate), tecloftalam, triazoxide, flusulfamide, diclomezine, methasulfocarb, cyflufenamid, metrafenone, pyriofenone, dodine, dodine free base, and flutianil.

(12) Agents having multiple activities: copper (copper salts), bordeaux mixture, copper hydroxide, copper naphthalate, copper oxide, copper oxychloride, copper sulfate, sulfur, sulfur products, calcium polysulfide, ferbam, mancozeb, maneb, mancopper, metiram, polycarbamate, propineb, thiram, zineb, ziram, captan, captafol, folpet, chlorothalonil, dichlofluanid, tolylfluanid, guazatine, iminoctadine triacetate, iminoctadine trialbesilate, anilazine, dithianon, quinomethionate, and fluoroimide.

(13) Other agents: DBEDC, fluor folpet, guazatine acetate, bis(8-quinolinolato) copper (II), propamidine, chloropicrin, cyprofuram, *Agrobacterium*, bethoxazin, diphenylamine, methyl isothiocyanate (MITC), mildiomycin, capsaicin, curfraneb, cyprosulfamide, dazomet, debacarb, dichlorophen, flumetover, fosetyl-calcium, fosetyl-sodium, irumamycin, natamycin, nitrothal isopropyl, oxamocarb, pyrrolnitrin, tebufloquin, tolnifanide, zarilamide, algophase, amicarthiazol, oxathiapiprolin, metiram zinc, benthiazole, trichlamide, uniconazole, oxyfenthiin, picarbutrazox, fenpicoxamid, dichlobentiazox, quinofumelin, thiuram, ambam, *Agrobacterium Radiobacter, Coniothyrium minitans, Pseudomonas fluorescens, Pseudomonas rhodesiae, Talaromyces flavus, Trichoderma atroviride, Erwinia carotovora* subsp. *carotovora, Bacillus simplex, Variovorax paradoxus*, and *Lactobacillus plantarum*.

Specific examples of plant growth regulators that can be mixed or used in combination with the formulation for controlling harmful organism of the present invention are listed below.

Abscisic acid, kinetin, benzylaminopurine, 1,3-diphenylurea, forchlorfenuron, thidiazuron, chlorfenuron, dihydrozeatin, gibberellin A, gibberellin A4, gibberellin A7, gibberellin A3,1-methylcyclopropane, N-acetyl aminoethoxyvinylglycine (alternative name: aviglycine), aminooxyacetate, silver nitrate, cobalt chloride, IAA, 4-CPA, cloprop, 2,4-D, MCPB, indole 3-butyrate, dichlorprop, phenothiol, 1-naphthyl acetamide, ethychlozate, cloxyfonac, maleic acid hydrazide, 2,3,5-triiodobenzoic acid, salicylic acid, methyl salicylate, (−)-jasmonic acid, methyl jasmonate, (+)-strigol, (+)-deoxystrigol, (+)-orobanchol, (+)-sorgolactone, 4-oxo-4-(2-phenylethyl)aminobutyric acid, ethephon, chlormequat, mepiquat chloride, benzyl adenine, 5-aminolevulinic acid, and daminozide.

[Formulation for Controlling Ectoparasites]

The formulation for controlling ectoparasites according to the present invention contains at least one compound selected from the diaryl azole compounds of the present invention as an active ingredient. The diaryl azole compounds of the present invention exhibit superior effects of controlling ectoparasites which are harmful with respect to animals and humans.

Examples of ectoparasites include mites, lice, fleas, mosquitoes, stable flies, flesh flies, and the like.

Examples of the host animals for which the formulation for controlling ectoparasites of the present invention include warm-blooded animals such as a pet animal such as a dog or a cat; a pet bird; a farm animal such as cattle, horse, pig, or sheep; a domestic fowl; and the like. In addition, honeybees, stag beetles, unicorn beetles may be mentioned.

The ectoparasites live on the host animals, especially live inside or upon warm-blooded animals. More specifically, the ectoparasites are parasitic in the back, armpit, underbelly, inner thigh and the like of the host animals and obtain nutritional sources such as blood, dandruff from the animals to live.

The formulation for controlling ectoparasites of the present invention can be applied by a known veterinary method (topical, oral, parenteral or subcutaneous administration). Examples of the method include a method for orally administering tablets, capsules and drinks mixed with the formulation for controlling ectoparasites to the animals; a method for administering to the animals by using an immersion liquid, suppository or injection (intramuscular, subcutaneous, intravenous, intraabdominal or the like); a method for topically administering an oil-based or aqueous liquid preparation by spraying, pouring on, spotting on or the like; a method for topically administering by attaching a collar, an ear tag or the like made by molding a mixture obtained by kneading the formulation for controlling ectoparasites with a resin to the animals; and the like.

Specific examples of the ectoparasites which can be prevented by the formulation for controlling ectoparasites according to the present invention are described below.

(1) Acari

Acari belonging to the Dermanyssidae family, acari belonging to the Macronyssidae family, acari belonging to the Laelapidae family, acari belonging to the Varroidae family, acari belonging to the Argasidae family, acari belonging to the Ixodidae family, acari belonging to the Psoroptidae family, acari belonging to the Sarcoptidae family, acari belonging to the Knemidokoptidae family, acari belonging to the Demodixidae family, acari belonging to the Trombiculidae family, and insect-parasitic acari such as *Coleopterophagus berlesei*.

(2) Phthiraptera Order

Lice belonging to the Haematopinidae family, lice belonging to the Linognathidae family, biting lice belonging to the Menoponidae family, biting lice belonging to the Philopteridae family, and biting lice belonging to the Trichodectidae family.

(3) Siphonaptera Order

Fleas belonging to the Pulicidae family, for example, *Ctenocephalides canis* and *Ctenocephalides felis* of *Ctenocephalides* spp.;

Fleas belonging to the Tungidae family, fleas belonging to the Ceratophyllidae family, and fleas belonging to the Leptopsyllidae family.

(4) Hemiptera Order.

(5) Harmful organism of Diptera order Mosquitoes belonging to the Culicidae family, black flies belonging to the Simuliidae family, punkie belonging to the Ceratopogonidae family, flies belonging to the Tabanidae family, flies belonging to the Muscidae family, tsetse flies belonging to the Glossinidae family, flesh flies belonging to the Sarcophagidae family, flies belonging to the Hippoboscidae family, flies belonging to the Calliphoridae family, and flies belonging to the Oestridae family;

[Endoparasite Controlling Formulation or Parasiticide]

An endoparasite controlling formulation or parasiticide of the present invention contains at least one compound selected from the diaryl azole compounds of the present invention as an active ingredient.

The parasites targeted by the endoparasite controlling formulation or parasiticide of the present invention live inside the bodies of host animals, and particularly inside the bodies of warm-blooded animals and fish (namely, endoparasites). Examples of host animals for which the endoparasite controlling formulation or parasiticide of the present invention is effective include warm-blooded animals such as humans, domestic mammals (for example, cows, horses, pigs, sheep, and goats and the like), experimental animals (for example, mice, rats, and gerbils and the like), pet animals (for example, hamsters, guinea pigs, dogs, cats, horses, squirrels, rabbits, and ferrets and the like), wild mammals and zoo mammals (for example, monkeys, foxes, deer, and buffalo and the like), domestic fowl (for example, turkeys, ducks, chickens, quail, and goose, and the like), and pet birds (for example, pigeons, parrots, myna birds, Java finches, parakeets, Bengalese finches, and canaries and the like); and fishes such as salmon, trout, and koi carp and the like. By controlling or exterminating the parasites, parasitic diseases carried by the parasites can be prevented or treated.

Examples of parasites that can be controlled or exterminated include those listed below.

(1) Dioctophymatida Nematodes (a) Kidney worms of the Dioctophymatidae family, for example, *Dioctophyma renale* of *Dioctophyma* spp.; and (b) Kidney worms of the Soboliphymatidae family, for example, *Soboliphyme abei* and *Soboliphyme baturini* of *Soboliphyme* spp.

(2) Trichocephalida Nematodes (a) Trichina worms of the Trichinellidae family, for example, *Trichinella spiralis* of *Trichinella* spp.; and (b) Whipworms of the Trichuridae family, for example, *Capillaria annulata*, *Capillaria contorta*, *Capillaria hepatica*, *Capillaria perforans*, *Capillaria plica* and *Capillaria suis* of *Capillaria* spp.; and *Trichuris vulpis*, *Trichuris discolor*, *Trichuris ovis*, *Trichuris skrjabini* and *Trichuris suis* of *Trichuris* spp.

(3) Rhabditida Nematodes

Threadworms of the Strongyloididae family, for example, *Strongyloides papillosus*, *Strongyloides planiceps*, *Strongyloides ransomi*, *Strongyloides suis*, *Strongyloides stercoralis*, *Strongyloides tumefaciens* and *Strongyloides ratti* of *Strongyloides* spp.

(4) Strongylida Nematodes

Hookworms of the Ancylostomatidae family, for example, *Ancylostoma braziliense*, *Ancylostoma caninum*, *Ancylostoma duodenale* and *Ancylostoma tubaeforme* of *Ancylostoma* spp.; *Uncinaria stenocephala* of *Uncinaria stenocephala*; and *Bunostomum phlebotomum* and *Bunostomum trigonocephalum* of *Bunostomum* spp.

(5) Strongylida Nematodes (a) Nematodes of the Angiostrongylidae family, for example, *Aelurostrongylus abstrusus* of *Aelurostrongylus* spp.; and *Angiostrongylus vasorum* and *Angiostrongylus cantonesis* of *Angiostrongylus* spp.;

(b) Nematodes of the Crenosomatidae family, for example, *Crenosoma aerophila* and *Crenosoma vulpis* of *Crenosoma* spp.;

(c) Nematodes of the Filaroididae family, for example, *Filaroides hirthi* and *Filaroides osleri* of *Filaroides* spp.;

(d) Lungworms of the Metastrongylidae family, for example, *Metastrongylus apri*, *Metastrongylus asymmetricus*, *Metastrongylus pudendotectus* and *Metastrongylus salmi* of *Metastrongylus* spp.; and (e) Gapeworms of the Syngamidae family, for example, *Cyathostoma bronchialis* of *Cyathostoma* spp.; and *Syngamus skrjabinomorpha* and *Syngamus trachea* of *Syngamus* spp.

(6) Strongylida Nematodes (a) Nematodes of the Molineidae family, for example, *Nematodirus filicollis* and *Nematodirus spathiger* of *Nematodirus* spp.;

(b) Nematodes of the Dictyocaulidae family, for example, *Dictyocaulus filarial* and *Dictyocaulus viviparus* of *Dictyocaulus* spp.;

(c) Nematodes of the Haemonchidae family, for example, *Haemonchus contortus* of *Haemonchus* spp.; and *Mecistocirrus digitatus* of *Mecistocirrus* spp.;

(d) Nematodes of the Haemonchidae family, for example, *Ostertagia ostertagi* of *Ostertagia* spp.;

(e) Nematodes of the Heligmonellidae family, for example, *Nippostrongylus braziliensis* of *Nippostrongylus* spp.; and (f) Nematodes of the Trichostrongylidae family, for example, *Trichostrongylus axei*, *Trichostrongylus colubriformis* and *Trichostrongylus tenuis* of *Trichostrongylus* spp.; *Hyostrongylus rubidus* of *Hyostrongylus* spp.; and *Obeliscoides cuniculi* of *Obeliscoides* spp.

(7) Strongylida Nematodes (a) Nematodes of the Chabertiidae family, for example, *Chabertia ovina* of *Chabertia* spp.; and *Oesophagostomum brevicaudatum*, *Oesophagostomum columbianum*, *Oesophagostomum dentatum*, *Oesophagostomum georgianum*, *Oesophagostomum maplestonei*, *Oesophagostomum quadrispinulatum*, *Oesophagostomum radiatum*, *Oesophagostomum venulosum* and *Oesophagostomum watanabei* of *Oesophagostomum* spp.;

(b) Nematodes of the Stephanuridae family, for example, *Stephanurus dentatus* of *Stephanurus* spp.; and (c) Nematodes of the Strongylidae family, for example, *Strongylus asini*, *Strongylus edentatus*, *Strongylus equinus* and *Strongylus vulgaris* of *Strongylus* spp.

(8) Oxyurida Nematodes

Nematodes of the Oxyuridae family, for example, *Enterobius anthropopitheci* and *Enterobius vermicularis* of *Enterobius* spp.; *Oxyuris equi* of *Oxyuris* spp.; and *Passalurus ambiguus* of *Passalurus* spp.

(9) Ascaridida Nemtaodes (a) Nematodes of the Ascaridiidae family, for example, *Ascaridia galli* of *Ascaridia* spp.;

(b) Nematodes of the Heterakidae family, for example, *Heterakis beramporia*, *Heterakis brevispiculum*, *Heterakis gallinarum*, *Heterakis pusilla* and *Heterakis putaustralis* of *Heterakis* spp.;

(c) Nematodes of the Anisakidae family, for example, *Anisakis simplex* of *Anisakis* spp.;

(d) Nematodes of the Ascarididae family, for example, *Ascaris lumbricoides* and *Ascaris suum* of *Ascaris* spp.; and *Parascaris equorum* of *Parascaris* spp.; and (e) Nematodes of the Toxocaridae family, for example, *Toxocara canis*, *Toxocara leonina*, *Toxocarasuum*, *Toxocara vitulorum* and *Toxocara cati* of *Toxocara* spp.

(10) Spirurida Nematodes (a) Nematodes of the Onchocercidae family, for example, *Brugia malayi*, *Brugia pahangi* and *Brugia patei* of *Brugia* spp.; *Dipetalonema reconditum* of *Dipetalonema* spp.; *Dirofilaria immitis* of *Dirofilaria* spp.; *Filaria oculi* of *Filaria* spp.; and *Onchocerca cervicalis*, *Onchocerca gibsoni* and *Onchocerca gutturosa* of *Onchocerca* spp.

(b) Nematodes of the Setariidae family, for example, *Setaria digitata*, *Setaria equina*, *Setaria labiatopapillosa* and *Setaria marshalli* of *Setaria* spp.; and *Wuchereria bancrofti* of *Wuchereria* spp.; and (c) Nematodes of the Filariidae family, for example, *Parafilaria multipapillosa* of *Parafilaria* spp.; and *Stephanofilaria assamensis*, *Stephanofilaria dedoesi*, *Stephanofilaria kaeli*, *Stephanofilaria okinawaensis* and *Stephanofilaria stilesi* of *Stephanofilaria* spp.

(11) Spirurida Nematodes (a) Nematodes of the Gnathostomatidae family, for example, *Gnathostoma doloresi* and *Gnathostoma spinigerum* of *Gnathostoma* spp.;

(b) Nematodes of the Habronematidae family, for example, *Habronema majus*, *Habronema microstoma* and *Habronema muscae* of *Habronema* spp.; and *Draschia megastoma* of *Draschia* spp.;

(c) Nematodes of the Physalopteridae family, for example, *Physaloptera canis*, *Physaloptera cesticillata*, *Physaloptera erdocyona*, *Physaloptera felidis*, *Physaloptera gemina*, *Physaloptera papilloradiata*, *Physaloptera praeputialis*, *Physaloptera pseudopraerutialis*, *Physaloptera rara*, *Physaloptera sibirica* and *Physaloptera vulpineus* of *Physaloptera* spp.;

(d) Nematodes of the Gongylonematidae family, for example, *Gongylonema pulchrum* of *Gongylonema* spp.;

(e) Nematodes of the Spirocercidae family, for example, *Ascarops strongylina* of *Ascarops* spp.; and (f) Nematodes of the Thelaziidae family, for example, *Thelazia callipaeda*, *Thelazia gulosa*, *Thelazia lacrymalis*, *Thelazia rhodesi* and *Thelazia skrjabini* of *Thelazia* spp.

[Formulation for Controlling Other Harmful Organisms]

In addition, the formulations for controlling harmful organisms of the present invention exhibit a superior effect for controlling other pests that have a sting or venom that can harm humans and animals, pests carrying various pathogens/pathogenic bacteria, and pests that impart a discomforting sensation to humans (such as toxic pests, sanitary insect pests, unpleasant insect pests).

Specific examples thereof are listed below.

(1) Hymenoptera Insect Pests

Sawflies of the Argidae family, wasps of the Cynipidae family, sawflies of the Diprionidae family, ants of the Formicidae family, wasps of the Mutillidae family, and wasps of the Vespidae family.

(2) Other Insect Pests

Blattodea, termites, Araneae, centipedes, millipedes, crustacea and *Cimex lectularius*.

The diaryl pyrazole compounds of the present invention possess superior insecticidal effects with respect to whiteflies, *Thrips*, planthoppers, Blattodea, *Phyllotreta striolata*, and the like, among the harmful organisms mentioned above.

EXAMPLES

Formulation Examples

Some examples of the formulations for controlling harmful organisms, insecticides, acaricides, formulations for controlling ectoparasites, or formulations for controlling or expelling endoparasites of the present invention are described below. The additives and the addition ratios are not limited to those in the examples and can be modified over a wide range. The term "part" in the formulation examples indicates "part by weight".

The formulation examples for agricultural and horticultural use and for paddy rice are described below.

(Formulation 1: Wettable Powder)

40 parts of a diaryl pyrazole compound of the present invention, 53 parts of diatomaceous earth, 4 parts of a higher alcohol sulfuric ester, and 3 parts of an alkylnaphthalene sulfonic acid salt were uniformly mixed and finely pulverized to obtain a wettable powder including 40% of an active ingredient.

(Formulation 2: Emulsion)

30 parts of the diaryl pyrazole compound of the present invention, 33 parts of xylene, 30 parts of dimethylformamide and 7 parts of a polyoxyethylene alkyl aryl ether were mixed and dissolved to obtain an emulsion including 30% of an active ingredient.

(Formulation 3: Granules)

5 parts of the diaryl pyrazole compound of the present invention, 40 parts of talc, 38 parts of clay, 10 parts of bentonite and 7 parts of sodium alkylsulfate were uniformly mixed and finely pulverized, followed by granulating into a granular shape having a diameter of 0.5 to 1.0 mm to obtain granules containing 5% of an active ingredient.

(Formulation 4: Granules)

5 parts of the diaryl pyrazole compound of the present invention, 73 parts of clay, 20 parts of bentonite, 1 part of sodium dioctyl sulfosuccinate and 1 part of potassium phosphate were thoroughly pulverized and mixed. Water was added thereto, and the mixture was kneaded well, followed by granulating and drying to obtain granules containing 5% of an active ingredient.

(Formulation 5: Suspension)

10 parts of the diaryl pyrazole compound according to the present invention, 4 parts of polyoxyethylene alkyl allyl ether, 2 parts of sodium polycarboxylate, 10 parts of glycerol, 0.2 parts of xanthan gum and 73.8 parts of water were mixed and wet-pulverized so as to have a grain size of 3 microns or less. Thereby, a suspension containing 10% of an active ingredient was obtained.

The formulation examples of the formulation for controlling ectoparasites, or the formulation for controlling or expelling endoparasites are described below.

(Formulation 6: Granulated Powder)

5 parts of the diaryl pyrazole compound of the present invention was dissolved in an organic solvent to obtain a solution. The solution mentioned above was sprayed on 94 parts of kaolin and 1 part of white carbon, followed by evaporating the solvent under reduced pressure. This type of granulated powder may be mixed with animal food.

(Formulation 7: Impregnating Formulation)

0.1 to 1 parts of the diaryl pyrazole compound of the present invention and 99 to 99.9 parts of peanut oil were uniformly mixed, and then filter-sterilized by means of a sterilizing filter.

(Formulation 8: Pour-on Formulation)

5 parts of the diaryl pyrazole compound of the present invention, 10 parts of a myristic ester and 85 parts of isopropanol were uniformly mixed to obtain a pour-on formulation.

(Formulation 9: Spot-On Formulation)

10 to 15 parts of the diaryl pyrazole compound of the present invention, 10 parts of a palmitic ester and 75 to 80 parts of isopropanol were uniformly mixed to obtain a spot-on formulation.

(Formulation 10: Spray Formulation)

1 part of the diaryl pyrazole compound of the present invention, 10 parts of propylene glycol and 89 parts of isopropanol were uniformly mixed to obtain a spray formulation.

Next, Examples of compounds are described to explain the present invention more specifically. It should be understood that the present invention is not limited to the following examples of compounds.

Example 1

Synthesis of 3-(ethylsulfonyl)-2-(5-methyl-4-(4-(trifluoromethoxy) phenyl)-1H-pyrazol-1-yl)-6-(1H-1,2,4-triazol-1-yl)pyridine (Compound No. 1-1)

(Step 1) Synthesis of ethyl 5-amino-1-(3-fluoropyridin-2-yl)-1H-pyrazole-4-carboxylate

[Chem. 6]

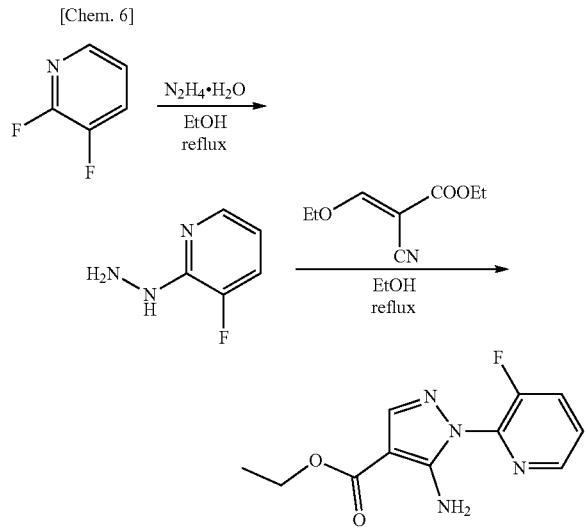

2,3-Difluoropyridine (2.4 g) was dissolved in ethanol (42 ml), and hydrazine hydrate (10.5 g) was added thereto. The mixture was stirred for 3 hours under heating and refluxing. The reaction solution mentioned above was concentrated, and water was poured into the obtained residue. The mixture was subjected to extraction with ethyl acetate. The obtained organic layer was dried over anhydrous magnesium sulfate, and filtered. The filtrate was concentrated under reduced pressure. The obtained residue (2.3 g) was dissolved in ethanol (31 ml), and ethyl (ethoxymethylene)cyanoacetate (3.1 g) was added thereto. The mixture was stirred overnight under heating and refluxing. The reaction solution mentioned above was concentrated, and water was poured into the obtained residue. The mixture was subjected to extraction with ethyl acetate. The obtained organic layer was dried over anhydrous magnesium sulfate, and filtered. The filtrate was concentrated under reduced pressure, and the obtained residue was purified by column chromatography with silica gel. Thereby, the objective product was obtained in an amount of 4.1 g (yield 91%). $^1$H-NMR of the objective product obtained is shown below.

$^1$H-NMR (400 MHz, CDCl$_3$): δ 8.26 (d, 1H), 7.84 (s, 1H), 7.66 (m, 1H), 7.28 (m, 1H), 6.92 (br s, 2H), 4.31 (q, 2H), 1.37 (t, 3H).

(Step 2) Synthesis of 1-(3-fluoropyridin-2-yl)-1H-pyrazol-5-amine

[Chem. 7]

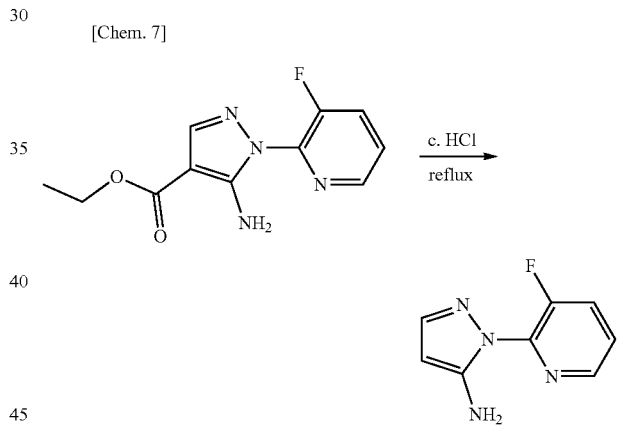

Ethyl 5-amino-1-(3-fluoropyridin-2-yl)-1H-pyrazol-4-carboxylate (2.1 g) was dissolved in concentrated hydrochloric acid (10 ml), and the mixture was stirred for 4 hours under heating and refluxing. The reaction solution mentioned above was added to water, and neutralized by adding potassium carbonate. Subsequently, the mixture was subjected to extraction with dichloromethane. The obtained organic layer was washed with a saturated aqueous solution of sodium chloride, dried over anhydrous magnesium sulfate, and then filtered. The filtrate was concentrated under reduced pressure. The obtained residue was purified by column chromatography with silica gel. Thereby, the objective product was obtained in an amount of 1.2 g (yield 77%). $^1$H-NMR of the objective product obtained is shown below.

$^1$H-NMR (400 MHz, CDCl$_3$): δ 8.24 (d, 1H), 7.64 (m, 1H), 7.52 (s, 1H), 7.24 (m, 1H), 5.60 (d, 1H), 5.23 (br s, 2H).

(Step 3) Synthesis of 4-bromo-1-(3-fluoropyridin-2-yl)-1H-pyrazol-5-amine

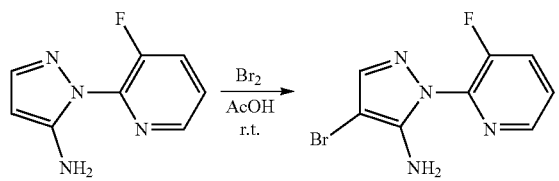

[Chem. 8]

1-(3-Fluoropyridin-2-yl)-1H-pyrazol-5-amine (1.2 g) was dissolved in acetic acid (6 ml), bromine (1.0 g) was dropped thereinto, and the reaction mixture was stirred for one hour at room temperature. The reaction solution was added to water, and neutralized by adding potassium carbonate. Subsequently, the reaction solution was subjected to extraction with ethyl acetate. The obtained organic layer was washed with a saturated aqueous solution of sodium chloride, dried over anhydrous magnesium sulfate, and then filtered. The filtrate was concentrated under reduced pressure, and purified by column chromatography with silica gel. Thereby, the objective product was obtained in an amount of 1.6 g (yield 93%). $^1$H-NMR of the objective product obtained is shown below.

$^1$H-NMR (400 MHz, CDCl$_3$): δ 8.25 (d, 1H), 7.65 (m, 1H), 7.52 (s, 1H), 7.27 (m, 1H), 5.38 (br s, 2H).

Step 4

Synthesis of 1-(3-fluoropyridin-2-yl)-4-(4-(trifluoromethoxy)phenyl)-1H-pyrazol-5-amine

[Chem. 9]

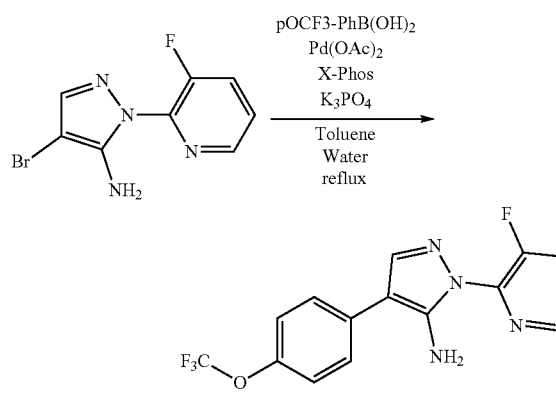

4-Bromo-1-(3-fluoropyridin-2-yl)-1H-pyrazol-5-amine (0.51 g) was dissolved in toluene (5 ml), and water (1.7 ml), 4-(trifluoromethoxy)phenylboronic acid (0.61 g), palladium (II) acetate (0.022 g), X-Phos (0.095 g), and potassium phosphate (0.84 g) were added thereto. The reaction mixture was stirred for 3 hours under an argon atmosphere and under heating and refluxing. The reaction solution mentioned above was added to water, and was subjected to extraction with ethyl acetate. The obtained organic layer was washed with a saturated aqueous solution of sodium chloride, dried over anhydrous magnesium sulfate, and then filtered. The filtrate was concentrated under reduced pressure, and purified by column chromatography with silica gel. Thereby, the objective product was obtained in an amount of 0.47 g (yield 70%). $^1$H-NMR of the objective product obtained is shown below.

$^1$H-NMR (400 MHz, CDCl$_3$): δ 8.28 (d, 1H), 7.71 (s, 1H), 7.68 (m, 1H), 7.48 (m, 2H), 7.29 (m, 2H), 5.51 (br s, 2H).

Step 5

Synthesis of 3-fluoro-2-(5-iodo-4-(4-(trifluoromethoxy)phenyl)-1H-pyrazol-1-yl)pyridine

[Chem. 10]

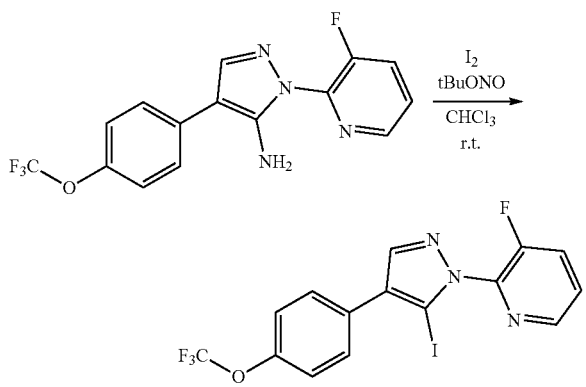

1-(3-Fluoropyridin-2-yl)-4-(4-(trifluoromethoxy)phenyl)-1H-pyrazol-5-amine (0.47 g) was dissolved in chloroform (10 ml), and then cooled to 0° C. Iodine (0.68 g) and tertiary butyl nitrite (0.30 ml) were added thereto, and the mixture was stirred for 8 hours at room temperature. The reaction solution mentioned above was added to water, and was subjected to extraction with ethyl acetate. The obtained organic layer was washed with a saturated aqueous solution of sodium chloride, dried over magnesium sulfate, and then filtered. The filtrate was concentrated under reduced pressure, and purified by column chromatography with silica gel. Thereby, the objective product was obtained in an amount of 0.56 g (yield 89%). $^1$H-NMR of the objective product obtained is shown below.

$^1$H-NMR (400 MHz, CDCl$_3$): δ 8.50 (d, 1H), 7.94 (s, 1H), 7.72 (m, 1H), 7.63 (m, 2H), 7.54 (m, 1H), 7.31 (m, 2H).

Step 6

Synthesis of 3-fluoro-2-(5-methyl-4-(4-(trifluoromethoxy)phenyl)-1H-pyrazol-1-yl)pyridine

[Chem. 11]

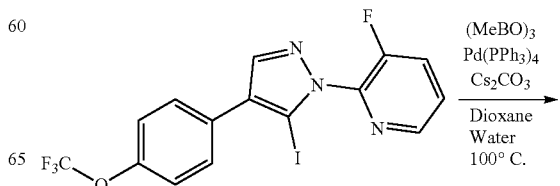

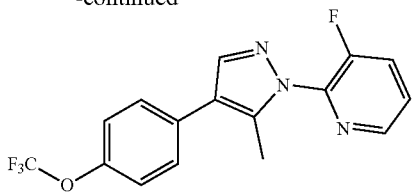

3-Fluoro-2-(5-iodo-4-(4-(trifluoromethoxy)phenyl)-1H-pyrazol-1-yl)pyridine (0.56 g) was dissolved in a solvent mixture of dioxane (13 ml) and water (1.5 ml), and trimethylboroxine (0.47 g), tetraxis(triphenylphosphine) palladium (0) (0.14 g), and cesium carbonate (1.2 g) were added thereto. The reaction mixture was stirred under a nitrogen atmosphere overnight at 100° C. The reaction solution mentioned above was added to water, and was subjected to extraction with ethyl acetate. The obtained organic layer was washed with a saturated aqueous solution of sodium chloride, dried over magnesium sulfate, and then filtered. The filtrate was concentrated under reduced pressure, and purified by column chromatography with silica gel. Thereby, the objective product was obtained in an amount of 0.33 g (yield 98%). $^1$H-NMR of the objective product obtained is shown below.

$^1$H-NMR (400 MHz, CDCl$_3$): δ 8.44 (d, 1H), 7.86 (s, 1H), 7.69 (m, 1H), 7.46 (m, 2H), 7.44 (m, 1H), 7.29 (m, 2H), 2.45 (s, 3H).

Step 7

Synthesis of 3-(ethylthio)-2-(5-methyl-4-(4-(trifluoromethoxy)phenyl)-1H-pyrazol-1-yl)pyridine

[Chem. 12]

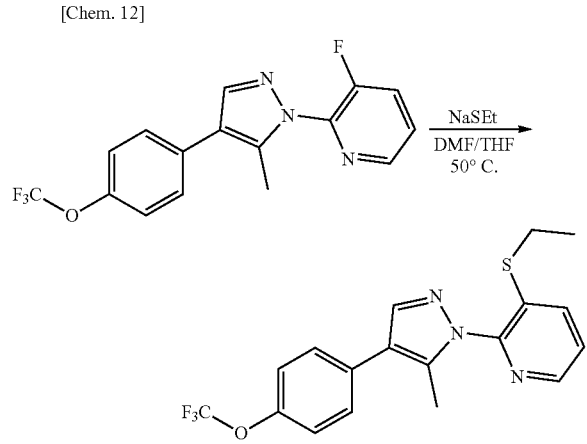

3-Fluoro-2-(5-methyl-4-(4-(trifluoromethoxy)phenyl)-1H-pyrazol-1-yl)pyridine (0.33 g) was dissolved in a solvent mixture of tetrahydrofuran (6 ml) and N,N-dimethylformamide (3 ml), and then stirred at room temperature. Sodium ethyl mercaptanate (80%, 0.15 g) was added thereto, and the mixture was stirred for 4 hours at 50° C. Water was poured into the reaction solution mentioned above, and subsequently, the mixture was subjected to extraction with ethyl acetate. The obtained organic layer was washed with a saturated aqueous solution of sodium chloride, dried over magnesium sulfate, and then filtered. The filtrate was concentrated under reduced pressure, and purified by column chromatography with silica gel. Thereby, the objective product was obtained in an amount of 0.34 g (yield 91%). $^1$H-NMR of the objective product obtained is shown below.

$^1$H-NMR (400 MHz, CDCl$_3$): δ 8.37 (dd, 1H), 7.83 (s, 1H), 7.78 (dd, 1H), 7.48 (m, 2H), 7.37 (dd, 1H), 7.27 (m, 2H), 2.91 (q, 2H), 2.38 (s, 3H), 1.32 (t, 3H).

Step 8

Synthesis of 3-(ethylsulfonyl)-2-(5-methyl-4-(4-(trifluoromethoxy)phenyl)-1H-pyrazol-1-yl)pyridine 1-oxide

[Chem. 13]

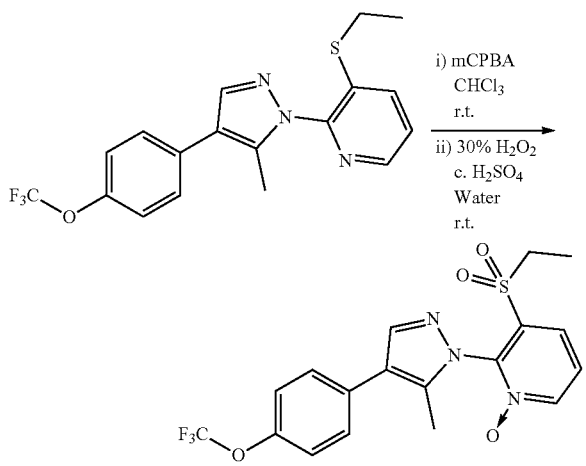

3-(Ethylthio)-2-(5-methyl-4-(4-(trifluoromethoxy)phenyl)-1H-pyrazol-1-yl) pyridine (0.34 g) was dissolved in chloroform (10 ml), and stirred at 0° C. Metachloroperbenzoic acid (70%, 0.64 g) was added thereto, and the mixture was stirred overnight at room temperature. The reaction solution was added to a solution mixture of a saturated aqueous solution of sodium hydrogencarbonate and a saturated aqueous solution of sodium thiosulfate, and was subjected to extraction with dichloromethane. The obtained organic layer was washed with a saturated aqueous solution of sodium chloride, dried over magnesium sulfate, and then filtered. The filtrate was concentrated under reduced pressure, and the obtained residue was dissolved in a solution mixture of water (0.33 ml) and concentrated sulfuric acid (1.0 ml). Hydrogen peroxide (30%, 0.11 ml) was added thereto, and the mixture was stirred overnight at room temperature. The reaction solution was added to water, neutralized by adding potassium carbonate, and subsequently subjected to extraction with ethyl acetate. The obtained organic layer was washed with a saturated aqueous solution of sodium chloride, dried over anhydrous magnesium sulfate, and then filtered. The filtrate was concentrated under reduced pressure, and purified by column chromatography with silica gel. Thereby, the objective product was obtained in an amount of 0.21 g (yield 55%). $^1$H-NMR of the objective product obtained is shown below.

$^1$H-NMR (400 MHz, CDCl$_3$): δ 8.54 (dd, 1H), 7.97 (dd, 1H), 7.93 (s, 1H), 7.60 (dd, 1H), 7.49 (m, 2H), 7.27 (m, 2H), 3.60-3.31 (m, 2H), 2.29 (s, 3H), 1.32 (t, 3H).

(Step 9) Synthesis of 6-chloro-3-(ethylsulfonyl)-2-(5-methyl-4-(4-(trifluoromethoxy)phenyl)-1H-pyrazol-1-yl)pyridine

[Chem. 14]

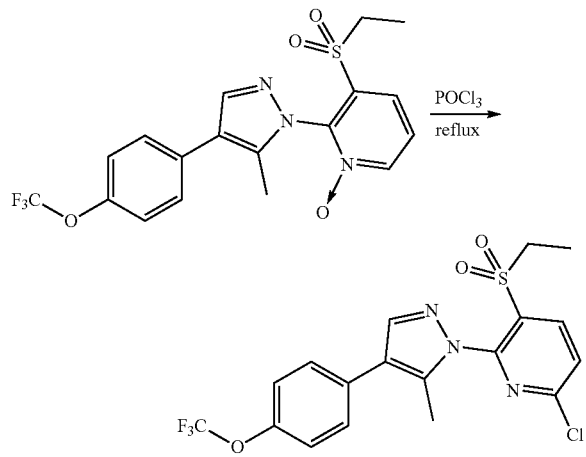

Phosphorus oxychloride (1.0 ml) was added to 3-(ethylsulfonyl)-2-(5-methyl-4-(4-(trifluoromethoxy)phenyl)-1H-pyrazol-1-yl)pyridine 1-oxide (0.21 g), and the mixture was stirred for 4 hours under heating and refluxing. The reaction solution mentioned above was added to water, and neutralized by adding sodium hydrogencarbonate. Subsequently, the reaction solution was subjected to extraction with ethyl acetate. The obtained organic layer was washed with a saturated aqueous solution of sodium chloride, dried over anhydrous magnesium sulfate, and then filtered. The filtrate was concentrated under reduced pressure, and the obtained residue was purified by column chromatography with silica gel. Thereby, the objective product was obtained in an amount of 0.13 g (yield 60%). $^1$H-NMR of the objective product obtained is shown below.

$^1$H-NMR (400 MHz, CDCl$_3$): δ 8.48 (d, 1H), 7.78 (s, 1H), 7.62 (d, 1H), 7.46 (m, 2H), 7.28 (m, 2H), 3.76 (q, 2H), 2.45 (s, 3H), 1.36 (t, 3H).

Step 10

Synthesis of 3-(ethylsulfonyl)-2-(5-methyl-4-(4-(trifluoromethoxy)phenyl)-1H-pyrazol-1-yl)-6-(1H-1,2,4-triazol-1-yl)pyridine (Compound No. 1-1)

[Chem. 15]

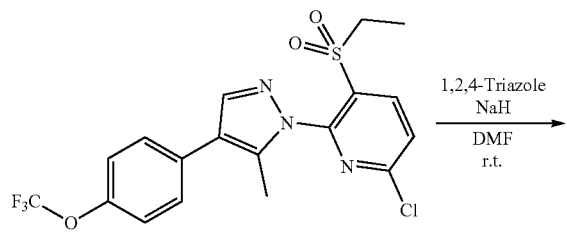

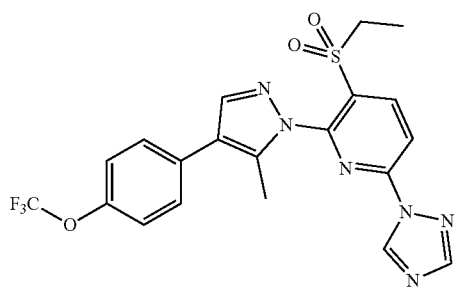

Sodium hydride (about 60%, 0.015 g) was added to and suspended in N,N-dimethylformamide (4 ml), and 1,2,4-triazole (0.024 g) was added thereto at 0° C. The mixture was stirred for 30 minutes. 6-Chloro-3-(ethyl sulfonyl)-2-(5-methyl-4-(4-(trifluoromethoxy)phenyl)-1H-pyrazol-1-yl) pyridine (0.13 g) was added thereto, and stirred for 2 hours at room temperature. The reaction solution mentioned above was added to water, and was subjected to extraction with ethyl acetate. The obtained organic layer was washed with a saturated aqueous solution of sodium chloride, dried over anhydrous magnesium sulfate, and then filtered. The filtrate was concentrated under reduced pressure, and the obtained residue was purified by column chromatography with silica gel. Thereby, the objective product was obtained in an amount of 0.10 g (yield 72%). $^1$H-NMR of the objective product obtained is shown below.

$^1$H-NMR (400 MHz, CDCl$_3$): δ 9.15 (s, 1H), 8.73 (d, 1H), 8.20 (d, 1H), 8.19 (s, 1H), 7.83 (s, 1H), 7.50 (m, 2H), 7.30 (m, 2H), 3.76 (q, 2H), 2.48 (s, 3H), 1.39 (t, 3H).

The compounds according to the present invention prepared by the same methods as those described in the aforementioned Examples are shown in Table 1. Table 1 shows the substituents of the compounds represented by Formula (I-1). The physical data of the compounds are described in the columns of "Physical property". As the physical property data, the property or the melting point (m. p.) are described. In the Tables, Me represents a methyl group, Et represents an ethyl group, and Boc represents a tert-butoxycarbonyl group.

[Chem. 16]

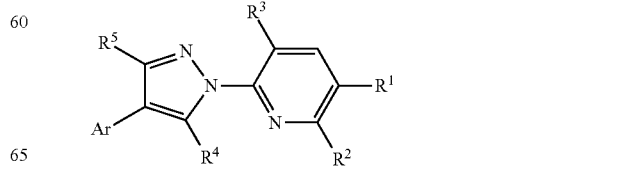

(I-1)

TABLE 1

| Compound No. | R¹ | R² | R³ | R⁴ | R⁵ | Ar | Physical property |
|---|---|---|---|---|---|---|---|
| 1-1 | H | 1H-1,2,4-triazol-1-yl | SO$_2$Et | Me | H | 4-OCF$_3$-phenyl | m.p.: 145-147 (° C.) |
| 1-2 | H | pyrimidin-2-yl | SO$_2$Et | Me | H | 4-OCF$_3$-phenyl | m.p.: 180-182 (° C.) |
| 1-3 | H | 3-CH$_3$-1H-1,2,4-triazol-1-yl | SO$_2$Et | Me | H | 4-OCF$_3$-phenyl | m.p.: 202-204 (° C.) |
| 1-4 | H | 3-NH$_2$-1H-1,2,4-triazol-1-yl | SO$_2$Et | Me | H | 4-OCF$_3$-phenyl | m.p.: 164-166 (° C.) |
| 1-5 | H | 5-NH$_2$-1H-1,2,4-triazol-1-yl | SO$_2$Et | Me | H | 4-OCF$_3$-phenyl | m.p.: 236-238 (° C.) |
| 1-6 | H | 3-Cl-1H-1,2,4-triazol-1-yl | SO$_2$Et | Me | H | 4-OCF$_3$-phenyl | m.p.: 238-240 (° C.) |
| 1-7 | H | 3-CF$_3$-1H-pyrazol-1-yl | SO$_2$Et | Me | H | 4-OCF$_3$-phenyl | m.p.: 160-164 (° C.) |
| 1-8 | H | pyrrolidin-1-yl | SO$_2$Et | Me | H | 4-OCF$_3$-phenyl | m.p.: 171-173 (° C.) |
| 1-9 | H | 4-oxopyridin-1(4H)-yl | SO$_2$Et | Me | H | 4-OCF$_3$-phenyl | amorphous |
| 1-10 | H | SMe | SO$_2$Et | Me | H | 4-OCF$_3$-phenyl | amorphous |
| 1-11 | H | SOMe | SO$_2$Et | Me | H | 4-OCF$_3$-phenyl | amorphous |
| 1-12 | H | SO$_2$Me | SO$_2$Et | Me | H | 4-OCF$_3$-phenyl | amorphous |
| 1-13 | H | pyrimidin-5-yl | SO$_2$Et | Me | H | 4-OCF$_3$-phenyl | amorphous |
| 1-14 | Cl | Cl | SO$_2$Et | Me | H | 4-OCF$_3$-phenyl | m.p.: 135-137 (° C.) |
| 1-15 | Cl | 1H-1,2,4-triazol-1-yl | SO$_2$Et | Me | H | 4-OCF$_3$-phenyl | m.p.: 158-161 (° C.) |
| 1-16 | H | 3-NH$_2$-1H-pyrazol-1-yl | SO$_2$Et | Me | H | 4-OCF$_3$-phenyl | m.p.: 178-181 (° C.) |
| 1-17 | H | cyclopropylamino | SO$_2$Et | Me | H | 4-OCF$_3$-phenyl | amorphous |
| 1-18 | H | 4-NH$_2$-1H-pyrazol-1-yl | SO$_2$Et | Me | H | 4-OCF$_3$-phenyl | m.p.: 87-90 (° C.) |
| 1-19 | H | 1H-1,2,4-triazol-1-yl | SO$_2$Et | Me | H | 6-CF$_2$CF$_3$-pyridin-3-yl | m.p.: 108-110 (° C.) |
| 1-20 | H | 3-CN-1H-1,2,4-triazol-1-yl | SO$_2$Et | Me | H | 4-OCF$_3$-phenyl | m.p.: 222-226 (° C.) |
| 1-21 | H | 3-NHBoc-1H-1,2,4-triazol-1-yl | SO$_2$Et | Me | H | 6-CF$_3$-pyridin-3-yl | m.p.: 138-141 (° C.) |
| 1-22 | H | 3-NHBoc-1H-1,2,4-triazol-1-yl | SO$_2$Et | Me | H | 1-SO$_2$CF$_3$-1H-pyrazol-4-yl | m.p.: 147-149 (° C.) |
| 1-23 | H | 3-NH$_2$-1H-1,2,4-triazol-1-yl | SO$_2$Et | Me | H | 6-CF$_3$-pyridin-3-yl | m.p.: 170-173 (° C.) |
| 1-24 | H | 3-NH$_2$-1H-1,2,4-triazol-1-yl | SO$_2$Et | Me | H | 1-SO$_2$CF$_3$-1H-pyrazol-4-yl | m.p.: 220-221 (° C.) |
| 1-25 | H | Cl | SO$_2$Et | Me | H | 4-OCF$_3$-phenyl | m.p.: 145-147 (° C.) |
| 1-26 | H | OH | SO$_2$Et | Me | H | 4-OCF$_3$-phenyl | m.p.: 78-80 (° C.) |
| 1-27 | H | 1H-imidazol-1-yl | SO$_2$Et | Me | H | 4-OCF$_3$-phenyl | m.p.: 175-177 (° C.) |
| 1-28 | H | 4-F-phenyl | SO$_2$Et | Me | H | 4-OCF$_3$-phenyl | m.p.: 132-134 (° C.) |
| 1-29 | H | OMe | SO$_2$Et | Me | H | 4-OCF$_3$-phenyl | m.p.: 109-111 (° C.) |
| 1-30 | H | OEt | SO$_2$Et | Me | H | 4-OCF$_3$-phenyl | m.p.: 105-107 (° C.) |
| 1-31 | H | OCH$_2$CF$_3$ | SO$_2$Et | Me | H | 4-OCF$_3$-phenyl | m.p.: 112-114 (° C.) |
| 1-32 | H | NHCOEt | SO$_2$Et | Me | H | 4-OCF$_3$-phenyl | m.p.: 75-77 (° C.) |
| 1-33 | 3,5-F$_2$-phenyl | H | SO$_2$Et | Me | H | 1-SO$_2$CF$_3$-1H-pyrazol-4-yl | m.p.: 160-162 (° C.) |
| 1-34 | H | 1H-1,2,4-triazol-1-yl | SO$_2$Et | NHCOCF$_3$ | H | 4-OCF$_3$-phenyl | m.p.: 230 (° C.) up |
| 1-35 | 3,5-F$_2$-phenyl | H | SO$_2$Et | NH$_2$ | H | 4-OCF$_3$-phenyl | m.p.: 208-210 (° C.) |
| 1-36 | H | OEt | SO$_2$Et | NH$_2$ | H | 4-OCF$_3$-phenyl | m.p.: 140-142 (° C.) |
| 1-37 | 3,5-F$_2$-phenyl | H | SO$_2$Et | NH$_2$ | H | 6-CF$_3$-pyridin-3-yl | m.p.: 231-234 (° C.) |
| 1-38 | 3,5-F$_2$-phenyl | H | SO$_2$Et | NH$_2$ | H | 4-SCF$_3$-phenyl | m.p.: 220-221 (° C.) |
| 1-39 | 3,5-F$_2$-phenyl | H | SO$_2$Et | NH$_2$ | H | 6-CF$_2$CF$_3$-pyridin-3-yl | m.p.: 222-224 (° C.) |
| 1-40 | 4-OCF$_3$-phenyl | H | SO$_2$Et | NH$_2$ | H | 4-OCF$_3$-phenyl | m.p.: 184-186 (° C.) |
| 1-41 | pyrimidin-2-yl | H | SO$_2$Et | NH$_2$ | H | 4-OCF$_3$-phenyl | m.p.: 212-214 (° C.) |
| 1-42 | pyrimidin-2-yl | H | SO$_2$Et | NH$_2$ | H | 4-CF$_3$-phenyl | m.p.: 250-252 (° C.) |
| 1-43 | pyrimidin-2-yl | H | SO$_2$Et | NH$_2$ | H | 4-CF$_2$CF$_3$-phenyl | m.p.: 250-252 (° C.) |
| 1-44 | 3,5-F$_2$-phenyl | H | SO$_2$Et | NH$_2$ | H | 4-CF$_3$-phenyl | m.p.: 233-236 (° C.) |
| 1-45 | pyrimidin-2-yl | H | SO$_2$Et | NH$_2$ | H | 6-CF$_3$-pyridin-3-yl | m.p.: 270-273 (° C.) |
| 1-46 | pyrimidin-2-yl | H | SO$_2$Et | NH$_2$ | H | 4-SCF$_3$-phenyl | m.p.: 201-205 (° C.) |
| 1-47 | pyrimidin-2-yl | H | SO$_2$Et | Me | H | 4-OCF$_3$-phenyl | m.p.: 177-180 (° C.) |
| 1-48 | pyrimidin-2-yl | H | SO$_2$Et | Me | H | 1-CHF$_2$-1H-pyrazol-4-yl | m.p.: 161-164 (° C.) |
| 1-49 | H | 1H-1,2,4-triazol-1-yl | SO$_2$Et | NH$_2$ | H | 4-OCF$_3$-phenyl | m.p.: 186-188 (° C.) |
| 1-50 | pyrimidin-2-yl | H | SO$_2$Et | NH$_2$ | H | 5-CF$_3$-pyridin-3-yl | m.p.: 256-258 (° C.) |
| 1-51 | 1H-1,2,4-triazol-1-yl | H | SO$_2$Et | NH$_2$ | H | 4-OCF$_3$-phenyl | m.p.: 159-161 (° C.) |
| 1-52 | pyrimidin-2-yl | H | SO$_2$Et | Me | H | 1-CF$_3$-1H-pyrazol-4-yl | m.p.: 163-165 (° C.) |
| 1-53 | 1H-1,2,4-triazol-1-yl | H | SO$_2$Et | NH$_2$ | H | 5-CF$_3$-pyridin-3-yl | m.p.: 223-224 (° C.) |
| 1-54 | 5-CF$_3$-pyridin-2-yl | H | SO$_2$Et | NH$_2$ | H | 4-OCF$_3$-phenyl | m.p.: 219-221 (° C.) |
| 1-55 | pyrimidin-2-yl | H | SO$_2$Et | Me | H | 1-CH$_2$CF$_3$-1H-pyrazol-4-yl | m.p.: 164-166 (° C.) |
| 1-56 | 5-CF$_3$-pyridin-2-yl | H | SO$_2$Et | NH$_2$ | H | 6-CF$_3$-pyridin-3-yl | m.p.: 244-246 (° C.) |

The $^1$H-NMR data (400 MHz, CDCl$_3$) of some compounds among the compounds described in Table 1 are shown in Table 2.

TABLE 2

| Compound No. | NMR data (ppm) |
|---|---|
| 1-9 | 8.71 (1H, d), 8.32-8.26 (2H, m), 7.82 (1H, s), 7.61 (1H, d), 7.51-7.46 (2H, m), 7.33-7.27 (2H, m), 6.58-6.51 (2H, m), 3.79 (2H, q), 2.49 (3H, s), 1.39 (3H, t). |
| 1-10 | 8.23 (1H, d), 7.78 (1H, s), 7.52-7.46 (2H, m), 7.41 (1H, d), 7.31-7.24 (2H, m), 3.68 (2H, q), 2.60 (3H, s), 2.43 (3H, s), 1.34 (3H, t). |
| 1-11 | 8.80 (1H, d), 8.35 (1H, d), 7.81 (1H, s), 7.50-7.43 (2H, m), 7.33-7.27 (2H, m), 3.79 (2H, q), 2.95 (3H, s), 2.41 (3H, s), 1.39 (3H, t). |
| 1-12 | 8.84 (1H, d), 8.32 (1H, d), 7.82 (1H, s), 7.52-7.44 (2H, m), 7.33-7.28 (2H, m), 3.88 (2H, q), 3.30 (3H, s), 2.50 (3H, s), 1.41 (3H, t). |
| 1-13 | 9.43 (2H, s), 9.37 (1H, s), 8.70 (1H, d), 8.07 (1H, d), 7.83 (1H, s), 7.55-7.48 (2H, m), 7.35-7.27 (2H, m), 3.81 (2H, q), 2.51 (3H, s), 1.40 (3H, t). |
| 1-17 | 8.23 (1H, d), 7.75 (1H, s), 7.49-7.42 (2H, m), 7.30-7.20 (2H, m), 6.91 (1H, d), 5.64 (1H, br s), 3.46 (2H, q), 2.69-2.59 (1H, br m), 2.36 (3H, s), 1.28 (3H, t), 0.97-0.88 (2H, m), 0.71-0.60 (2H, m). |

As described above, the diaryl pyrazole compounds according to the present invention can be easily produced by using known chemical reactions as described in the Examples mentioned above. It can be easily understood by a person having ordinary skill in the art from the descriptions of the specification of the present application that other compounds which are not particularly shown in the specification of the present application, that is, compounds having various substituted groups as long as they do not exceed the significance and the scope of the present invention, can be produced by means of the methods mentioned above and the like and can be used.

[Biological Tests]

The following Test Examples demonstrate that the diaryl pyrazole compounds of the present invention (hereinafter, referred to as "compounds of the present invention") are useful as active ingredients of the formulations for controlling harmful organisms, and of the formulations for controlling ectoparasites. The term "part" is based on weight.

(Preparation of Emulsion for Test)

5 parts of the compound of the present invention, 93.6 parts of dimethylformamide and 1.4 parts of polyoxyethylene alkyl aryl ether were mixed and dissolved to prepare Emulsion (I) including 5% of an active ingredient.

An insect mortality rate and a controlling rate were calculated by the numerical equations shown below.

Insect mortality rate(%)={(Number of dead insects)/(Number of sample insects)}×100

Controlling rate={1−(Nt)/(Nc)}×100 wherein
Nt: number of parasites in spray-treated area; and
Nc: number of parasites in non-treated area (Test Example 1) Efficacy Test Against *Mythimna separata*

0.8 g of a commercially available artificial feed (Insecta LFS, manufactured by Nosan Corporation) and 1 μl of Emulsion (I) were mixed thoroughly, and 0.2 g of the resulting mixture was placed in each of the treatment areas of a plastic test container (volume: 1.4 ml) to complete preparation of a test feed.

Two second-instar larvae of *Mythimna separata* were inoculated into each treatment area, and the test container was sealed with a plastic lid. The sealed container was placed in a thermostatic chamber at 25° C., and the insect mortality rate and the amount of feed consumed were determined on the fifth day. The test was performed twice. In addition, a test performed under the same conditions as those described above, but with the exception of excluding the compound of the present invention from the aforementioned Emulsion (I), was used as a control.

Efficacy tests against *Mythimna separata* were conducted for the compounds shown in Table 3. For all of the compounds, the mortality rate against *Mythimna separata* was 100%, or the amount of feed consumed was 10% or less of the amount of feed consumed in the control.

TABLE 3

| |
|---|
| 1-1 |
| 1-2 |
| 1-3 |
| 1-4 |
| 1-5 |
| 1-6 |
| 1-7 |
| 1-8 |
| 1-9 |
| 1-13 |
| 1-15 |
| 1-16 |
| 1-17 |
| 1-19 |
| 1-23 |
| 1-27 |
| 1-30 |
| 1-31 |
| 1-33 |
| 1-35 |
| 1-36 |
| 1-37 |
| 1-38 |
| 1-39 |
| 1-40 |
| 1-41 |
| 1-42 |
| 1-43 |
| 1-44 |
| 1-45 |
| 1-46 |
| 1-47 |
| 1-48 |
| 1-50 |
| 1-51 |
| 1-52 |
| 1-55 |
| 1-56 |

(Test Example 2) Efficacy Test Against *Spodoptera litura*

Emulsion (I) was diluted with water so that the concentration of the compound of the present invention was 125 ppm. Cabbage leaves were soaked in the diluted liquid for 30 seconds. Subsequently, the cabbage leaves were put on Petri dishes, followed by inoculating 5 second-instar larvae of *Spodoptera litura*. The Petri dishes were placed in a thermostatic chamber at a temperature of 25° C. and humidity of 60%. Mortality was investigated 6 days after inoculation, and the insect mortality rate was calculated. The test was performed twice.

The efficacy test against *Spodoptera litura* was carried out for the compounds shown in Table 4. All of the compounds demonstrated an 80% or more insect mortality rate against *Spodoptera litura*.

TABLE 4

| |
|---|
| 1-4 |
| 1-5 |
| 1-6 |
| 1-35 |
| 1-37 |
| 1-40 |
| 1-41 |
| 1-42 |
| 1-43 |
| 1-46 |
| 1-47 |
| 1-51 |
| 1-54 |

(Test Example 3) Efficacy Test Against *Plutella xylostella*

Emulsion (I) was diluted with water so that the concentration of the compound of the present invention was 125 ppm. Cabbage leaves were soaked in the diluted liquid for 30 seconds. Subsequently, the cabbage leaves were put on Petri dishes, followed by inoculating 5 second-instar larvae of *Plutella xylostella*. The Petri dishes were placed in a thermostatic chamber at a temperature of 25° C. and humidity of 60%. Mortality was investigated 3 days after inoculation, and the insect mortality rate was calculated. The test was performed twice.

The efficacy test against *Plutella xylostella* was carried out for the compounds shown in Table 5. All of the compounds demonstrated an 80% or more mortality rate against *Plutella xylostella*.

TABLE 5

| |
|---|
| 1-1 |
| 1-2 |
| 1-3 |
| 1-4 |
| 1-5 |
| 1-6 |
| 1-9 |
| 1-13 |
| 1-17 |
| 1-19 |
| 1-23 |
| 1-27 |
| 1-30 |
| 1-33 |
| 1-35 |
| 1-36 |
| 1-37 |
| 1-39 |
| 1-40 |
| 1-41 |
| 1-42 |
| 1-43 |
| 1-46 |
| 1-47 |
| 1-48 |
| 1-49 |
| 1-50 |
| 1-51 |
| 1-52 |
| 1-54 |
| 1-55 |

(Test Example 4) Efficacy Test Against *Aphis gossypii*

Emulsion (I) was diluted with water so that the concentration of the compound of the present invention was 125 ppm. Cucumbers were raised in No. 3 pots and the first leaves were inoculated with nymphs of *Aphis gossypii*. The diluted emulsion mentioned above was sprayed onto the cucumber seedlings. The aforementioned cucumber seedlings were then placed in a thermostatic chamber with a temperature of 25° C. and humidity of 60%. Mortality was investigated 4 days after spraying was carried out, and the insect mortality rate of *Aphis gossypii* was calculated. The test was performed twice.

The efficacy test against *Aphis gossypii* was carried out for the compounds according to the compound numbers shown in Table 6. All of the compounds demonstrated an 80% or more mortality rate against *Aphis gossypii*.

TABLE 6

| |
|---|
| 1-1 |
| 1-2 |
| 1-3 |
| 1-4 |

(Test Example 5) Efficacy Test Against *Aphis craccivora*

Black-eyed pea plants were raised in No. 3 pots and the primary leaves were inoculated with nymphs of *Aphis craccivora*. Emulsion (I) was diluted with water so that the concentration of the compound of the present invention was 125 ppm. Subsequently, the aforementioned diluted liquid was sprayed on the black-eyed pea plants on which the nymphs of *Aphis craccivora* were parasitic. The aforementioned black-eyed pea plants were then placed in a thermostatic chamber with a temperature of 25° C. and humidity of 60%. Mortality was investigated 4 days after spraying was carried out, and the insect mortality rate of *Aphis craccivora* was calculated. The test was performed twice.

The efficacy test against *Aphis craccivora* was carried out for the compounds shown in Table 7. All of the compounds demonstrated an 80% or more mortality rate against *Aphis craccivora*.

TABLE 7

| |
|---|
| 1-1 |
| 1-2 |
| 1-3 |
| 1-13 |
| 1-30 |
| 1-31 |
| 1-51 |
| 1-52 |

(Test Example 6) Efficacy Test Against *Bemisia tabaci*

Emulsion (I) was diluted with water so that the concentration of the compound of the present invention was 125 ppm, and subsequently, the diluted liquid was sprayed on young seedlings of tomato, followed by air-drying. On the day of the spraying, adult *Bemisia tabaci* were released to the seedlings so as to lay eggs. The number of parasitic larvae was counted 12 days after the spraying. The controlling (prevention) rate was calculated. The test was performed twice.

The efficacy test against *Bemisia tabaci* was carried out for the compounds shown in Table 8. All of the compounds demonstrated an 80% or more next-generation controlling rate.

TABLE 8

| |
|---|
| 1-1 |
| 1-2 |
| 1-13 |
| 1-15 |

(Test Example 7) Efficacy Test Against *Phyllotreta striolata*

Emulsion (I) was diluted with water so that the concentration of the compound of the present invention was 125 ppm, to prepare a diluted liquid for testing. The aforementioned diluted liquid was sprayed on bok-choi seedlings (7$^{th}$ major leaf-development period) planted in No. 3 pots. After the bok-choi seedlings were subjected to air-drying, the seedlings were placed in plastic cups, followed by inoculating 10 adult *Phyllotreta striolata*. The plastic cups were stored in a thermostatic chamber at a temperature of 25° C. and humidity of 65%. Mortality was investigated 7 days after inoculation, and the insect mortality rate was calculated. The test was performed twice.

The efficacy test against adult *Phyllotreta striolata* was carried out for the compounds shown in Table 9. All of the compounds demonstrated an 80% or more mortality rate against adult *Phyllotreta striolata*.

TABLE 9

| |
|---|
| 1-1 |
| 1-2 |
| 1-3 |
| 1-4 |
| 1-5 |
| 1-6 |
| 1-9 |
| 1-13 |
| 1-16 |
| 1-19 |
| 1-30 |
| 1-33 |
| 1-35 |
| 1-36 |
| 1-41 |
| 1-42 |
| 1-43 |
| 1-46 |
| 1-47 |
| 1-48 |
| 1-49 |
| 1-50 |
| 1-51 |
| 1-52 |

(Test Example 8) Efficacy Test Against *Phyllotreta striolata*

Emulsion (I) was diluted with water so that the concentration of the compound of the present invention was 8 ppm, to prepare a diluted liquid for testing. The aforementioned diluted liquid was sprayed on bok-choi seedlings (7$^{th}$ major leaf-development period) planted in No. 3 pots. After the bok-choi seedlings were subjected to air-drying, the seedlings were placed in plastic cups, followed by inoculating 10 adult *Phyllotreta striolata*. The plastic cups were stored in a thermostatic chamber at a temperature of 25° C. and humidity of 65%. Mortality was investigated 7 days after inoculation, and the insect mortality rate was calculated. The test was performed twice.

The efficacy test against adult *Phyllotreta striolata* was carried out for the compounds shown in Table 10. All of the compounds demonstrated an 80% or more mortality rate against adult *Phyllotreta striolata*.

TABLE 10

| |
|---|
| 1-1 |
| 1-2 |
| 1-3 |
| 1-4 |
| 1-5 |
| 1-6 |
| 1-9 |
| 1-13 |
| 1-19 |
| 1-30 |
| 1-33 |
| 1-35 |
| 1-36 |
| 1-41 |
| 1-42 |
| 1-43 |
| 1-46 |
| 1-47 |
| 1-48 |
| 1-49 |
| 1-50 |
| 1-51 |
| 1-52 |

(Test Example 9) Efficacy Test Against *Thrips palmi*

Inoculation of 10 adult *Thrips palmi* on cucumber seedlings was carried out. Emulsion (I) was diluted with water so that the concentration of the compound of the present invention was 125 ppm. The aforementioned diluted liquid was sprayed on the cucumber seedlings, followed by air-drying. The number of parasitic larvae was calculated 7 days after the spraying, and the controlling (prevention) rate was calculated. The test was performed twice.

The efficacy test against *Thrips palmi* was carried out for the compounds shown in Table 11. All of the compounds demonstrated an 80% or more next-generation controlling rate.

TABLE 11

| |
|---|
| 1-1 |
| 1-2 |
| 1-3 |
| 1-4 |
| 1-19 |
| 1-49 |
| 1-52 |

(Test Example 10) Efficacy Test Against *Thrips palmi*

Inoculation of 10 adult *Thrips palmi* on cucumber seedlings was carried out. Emulsion (I) was diluted with water so that the concentration of the compound of the present invention was 31 ppm. The aforementioned diluted liquid was sprayed on the cucumber seedlings, followed by air-drying. The number of parasitic larvae was calculated 7 days after the spraying, and the controlling (prevention) rate was calculated. The test was performed twice.

The efficacy test against *Thrips palmi* was carried out for the compounds shown in Table 12. All of the compounds demonstrated an 80% or more next-generation controlling rate.

TABLE 12

| |
|---|
| 1-1 |
| 1-2 |
| 1-3 |
| 1-4 |
| 1-19 |
| 1-49 |
| 1-52 |

(Test Example 11) Efficacy Test Against *Culex pipiens molestus*

Emulsion (I) was diluted with water so that the concentration of the compound of the present invention was 10 ppm, to prepare a chemical liquid for testing. 20 first-instar larvae of *Culex pipiens molestus* were released in 100 mL of the chemical liquid. After one day, the number of dead insects was counted, and the insect mortality rate was calculated. The test was performed twice.

The efficacy test against first-instar larvae of *Culex pipiens molestus* was carried out for the compounds shown in Table 13. All of the compounds demonstrated a 100% mortality rate against the first-instar larvae of *Culex pipiens molestus*.

TABLE 13

| |
|---|
| 1-1 |
| 1-2 |
| 1-3 |
| 1-4 |
| 1-5 |
| 1-6 |
| 1-7 |
| 1-8 |
| 1-9 |
| 1-10 |
| 1-13 |
| 1-15 |
| 1-16 |
| 1-21 |
| 1-22 |
| 1-23 |
| 1-24 |
| 1-45 |
| 1-46 |
| 1-50 |
| 1-51 |
| 1-52 |

(Test Example 12) Efficacy Test Against *Nilaparvata lugens*

Emulsion (I) was diluted with water so that the concentration of the compound of the present invention was 125 ppm. Rice seedlings were soaked in the diluted liquid for 30 seconds, and subjected to air-drying. Subsequently, the rice seedlings were placed in plastic cases, followed by inoculating 5 second-instar larvae of *Nilaparvata lugens*. The plastic cases were placed in a thermostatic chamber at a temperature of 25° C. and humidity of 65%. Mortality was investigated 7 days after inoculation, and the insect mortality rate was calculated. The test was performed twice.

The efficacy test against *Nilaparvata lugens* was carried out for the compounds shown in Table 14. All of the compounds demonstrated an 80% or more mortality rate against *Nilaparvata lugens*.

TABLE 14

| |
|---|
| 1-1 |
| 1-2 |
| 1-4 |
| 1-13 |

(Test Example 12) Efficacy Test Against *Mythimna separata* (Seed Treatment Test)

0.1 g of each of the compounds of the present invention was diluted with 2 mL of acetone to prepare a chemical liquid for test. 10 g of wheat seeds were added to the chemical liquid for test and air-dried, followed by seedling 100 seeds in a planter. After keeping the planter in a warm room with a temperature of 25° C. for 7 days, 100 first-instar larvae of *Mythimna separata* were released in the planter. The planter was kept in a warm room with a temperature of 25° C., the number of living *Mythimna separata* was investigated after 3 days had passed, and the controlling (prevention) rate was calculated. The test was performed twice.

The efficacy test against the first-instar larvae of *Mythimna separata* was carried out for the compounds shown in Table 15. As a result, all of the compounds demonstrated an 80% or more controlling rate against the first-instar larvae of *Mythimna separata*.

TABLE 15

| |
|---|
| 1-1 |
| 1-2 |
| 1-48 |

The compounds selected at random among the compounds according to the present invention exhibit the effects described above. For this reason, it can be understood that the compounds of the present invention including those which cannot be demonstrated above have effects of controlling harmful organisms, and in particular, acaricidal effects, insecticidal effects and the like. In addition, it can also be understood that the compounds of the present invention have effects on ectoparasites and the like which harm humans and animals.

INDUSTRIAL APPLICABILITY

A diaryl pyrazole compound which has superior activity for controlling harmful organisms, and in particular, superior insecticidal activity and/or acaricidal activity, which exhibits superior safety, and can be industrially-advantageously synthesized can be provided, and also a formulation for controlling harmful organisms containing the same as an active ingredient can be provided. In addition, a formulation for controlling ectoparasites or a formulation for controlling or expelling endoparasites which contains the same as an active ingredient can be provided.

What is claimed is:

1. A compound represented by Formula (I) or a salt thereof

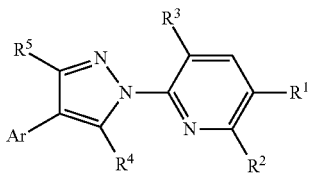

(I)

wherein
each of $R^1$ and $R^2$ independently represents a hydrogen atom, a substituted or unsubstituted C6-10 aryl group, or a substituted or unsubstituted 3- to 6-membered heterocyclyl group, with the proviso that in the case of $R^2$ being a hydrogen atom, $R^1$ is a substituted or unsubstituted C6-10 aryl group, or a substituted or unsubstituted 3- to 6-membered heterocyclyl group, and in the case of $R^1$ being a hydrogen atom, $R^2$ is a substituted or unsubstituted C6-10 aryl group, or a substituted or unsubstituted 3- to 6-membered heterocyclyl group,
wherein the substituted group on the "C6-10 aryl group" or "3- to 6-membered heterocyclyl group" of $R^1$ and $R^2$ is a halogeno group, a C1-6 alkyl group, a C1-6 haloalkyl group, a C1-6 haloalkoxy group, an amino group, a mono C1-6 alkoxy carbonyl amino group, a cyano group, or an oxo group,
$R^3$ represents a C1-6 alkylsulfonyl group,
$R^4$ represents C1-6 alkyl group, or a substituted or unsubstituted amino group,
wherein the substituted amino group of $R^4$ is a C1-6 alkyl amino group, a C3-8 cycloalkyl amino group, a C1-6 alkyl carbonylamino group, a mono(C1-6 alkoxy carbonyl) amino group, or a di(C1-6 alkoxy carbonyl) amino group,
$R^5$ represents a hydrogen atom, and
Ar represents a substituted or unsubstituted C6-10 aryl group, or a substituted or unsubstituted, 5- to 6-membered heteroaryl group,
wherein the substituted group of "C6-10 aryl group" and "5- to 6-membered heteroaryl group" of Ar is a C1-6 haloalkyl group, a C1-6 haloalkoxy group, a C1-6 haloalkylthio group, or a C1-6 haloalkylsulfonyl group.

2. A formulation for controlling harmful organisms, containing at least one compound selected from the group consisting of the compounds as recited in claim 1, and salts thereof, as an active ingredient.

3. An insecticidal formulation or an acaricidal formulation, containing at least one compound selected from the group consisting of the compounds as recited in claim 1, and salts thereof, as an active ingredient.

4. A formulation for controlling ectoparasites, containing at least one compound selected from the group consisting of the compounds as recited in claim 1, and salts thereof, as an active ingredient.

5. A formulation for controlling endoparasites or for expelling endoparasites, containing at least one compound selected from the group consisting of the compounds as recited in claim 1, and salts thereof, as an active ingredient.

* * * * *